United States Patent [19]

Hudspeth et al.

[11] 4,116,228

[45] Sep. 26, 1978

[54] RESPIRATION DATA ACQUISITION, CONVERSION AND DISPLAY SYSTEM

[75] Inventors: Emmett L. Hudspeth; Philip C. Richardson; John L. Neathery, Jr.; Jerald P. Dykstra; Allen D. Boger, Jr.; William B. Sims, Jr.; Glenn E. Hunt; Tony M. Quisenberry, all of Austin, Tex.

[73] Assignee: United States Surgical Corporation, Stamford, Conn.

[21] Appl. No.: 704,450

[22] Filed: Jul. 12, 1976

Related U.S. Application Data

[62] Division of Ser. No. 627,654, Oct. 31, 1975, which is a division of Ser. No. 385,699, Aug. 6, 1973, Pat. No. 3,940,742.

[51] Int. Cl.$^2$ ............................ A61B 5/08; A61B 5/02
[52] U.S. Cl. ............................ 128/2 R; 128/DIG. 29; 128/2.05 T; 128/2 H
[58] Field of Search .......... 128/2 R, DIG. 29, 2.05 P, 128/2.05 T, 2.05 R, 2.06 F

[56] References Cited

U.S. PATENT DOCUMENTS

| 3,316,902 | 5/1967 | Winchel et al. | 128/DIG. 29 UX |
| 3,602,806 | 8/1971 | Czekajewski | 128/DIG. 29 UX |
| 3,661,147 | 5/1972 | Mason et al. | 128/2.05 T |
| 3,742,937 | 7/1973 | Manuel et al. | 128/2.05 T |
| 3,766,908 | 10/1973 | Haynes | 128/2 H |
| 3,773,038 | 11/1973 | Smith et al. | 128/2.06 F |
| 3,807,388 | 4/1974 | Orr et al. | 128/2.05 P X |

OTHER PUBLICATIONS

Hershberg, P. I., et al., *Amer. Journ. of Med. Electronics;* 1963, Jul.-Sep., pp. 207-211.

*Primary Examiner*—Kyle L. Howell
*Attorney, Agent, or Firm*—Fleit & Jacobson

[57] ABSTRACT

Respiration data is measured and converted into a series of electrical output pulses, the frequency of which is related to the respiration rate. The output pulses trigger "on" and "off" a timing device, and the average time of a respiration cycle is then converted into a respiration rate and displayed. The timing device includes a means for delaying a first specified number of output pulses before beginning the sampling period and registering a count of clock pulses which represents the time period of a second specified number of the output pulses occurring subsequently to the first specified number of output pulses.

3 Claims, 25 Drawing Figures

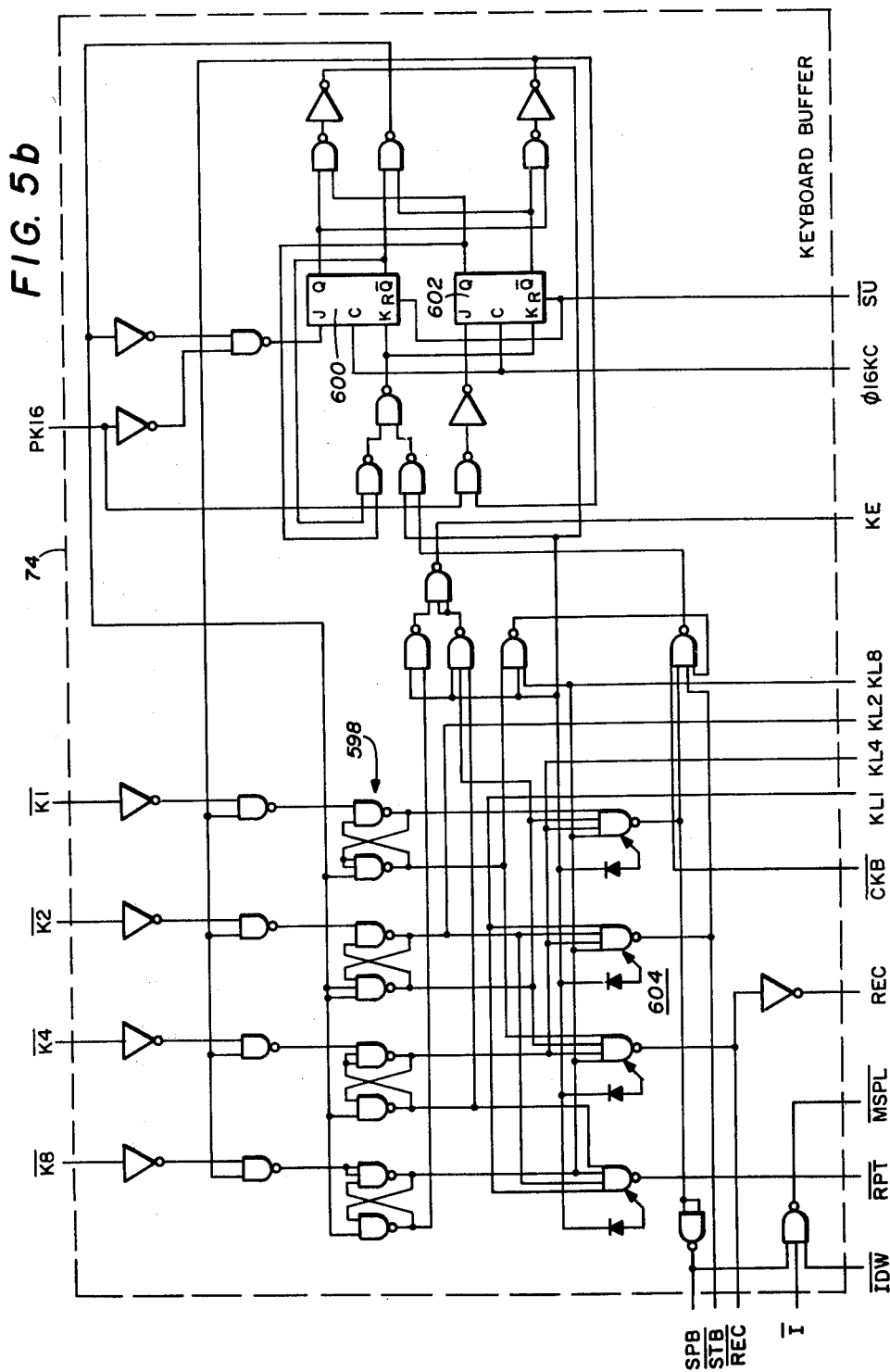

FIG. 5ℓ

RESPIRATION DATA ACQUISITION, CONVERSION AND DISPLAY SYSTEM

This is a division of application Ser. No. 627,654, filed Oct. 31, 1975, which is a division of application Ser. No. 385,699, filed Aug. 6, 1973 now U.S. Pat. No. 3,940,742.

This invention relates to an acquisition unit for acquiring data relating to one or more physiological variables from a patient, displaying the data digitally and, upon operator approval, recording the data in an internal memory. Further, the invention relates to a data printer responsive to data stored in an acquisition unit for a display presentation.

In the art of medical practice, it has been found desirable, under certain conditions, to maintain a substantially running record of certain body functions, such as for example, body temperature, pulse rate and respiration rate; these three comprising the basic body functions to be recorded. Heretofore, this vigilance has ordinarily been maintained by the nursing staff of the hospitals or other available attendants, who periodically observe and manually record the condition of the patient in accordance with a predetermined schedule. This observation and manual recording is a time consuming technique which lends itself to erroneous recording and analysis of a patient's body functions. Remedial measures taken after discovery of previously recorded erroneous data during the next period of inspection are often too late for the patient's condition.

The present invention provides for the automatic acquisition of data relating to a patient's body functions and provides an instrument that generates readily recordable signals accurately portraying temperature, respiration rate, pulse rate and additional data as desired. An important feature of the present invention resides in the use of a light weight, portable, battery operated acquisition unit having an internal memory for storing acquired data. The acquisition unit utilizes a temperature and respiration rate probe as described in the copending patent application of Emmett L. Hudspeth et al, filed Apr. 2, 1973, Ser. No. 346,952, assigned to the assignee of the present invention. In addition, the acquisition unit utilizes a standard pulse rate transducer for acquiring data relating to this body function. Thus, the nursing staff or other available attendant merely performs a mechanical task of placing the desired body function probe in or about a patient and operates the acquisition unit for acquiring desired data.

In the field of medical care, accuracy of collected data relating to the body functions of a patient is of significant importance. Erroneous data, whether collected manually or automatically, presents the possibility of an incorrect diagnosis of a patient's condition thereby leading to an erroneous prescription of remedial action. Another feature of the present invention allows the operator of the data acquisition unit to override the automatically generated data with manually generated data. In this situation, only the manually generated data is transferred to the acquisition unit memory and the automatic data is discarded. For future identification of the manually generated data, as opposed to the automatically generated data, the memory location containing the manual data also contains a highlighting code. This code, when subsequently observed along with the accompanying data information, indicates that the operator exercised individual judgment in observing a patient's condition.

A problem often encountered when using portable battery powered recording equipment is that the failure of the power supply nullifies or distorts previously recorded data. If this condition is observed, the faulty or erroneous data may be disregarded thus avoiding serious consequences that could result from the reliance upon such data. That particular series of data will, however, be lost and cannot be recovered. A more serious consequence is that the faulty or erroneous data is not recognized as such and is relied upon in diagnosing a patient's condition. Still another feature of the present invention is the use of an automatic data acquisition unit incorporating circuitry for monitoring the condition of a battery supply and for restricting the unit's use when the supply drops below a first threshold. In this mode of operation of the acquisition unit, all data previously stored in the internal memory is maintained for future recovery and utilization. If the battery supply power decreases below a second threshold level, the internal memory is deactivated and the stored data is lost, thereby preventing reliance on unreliable data.

Data acquired and stored in the internal memory of the acquisition unit of the present invention is transferred to a data printer that provides individual patient printouts containing all the body function data associated with a particular patient. The data printer transfers all the body function data for a particular patient into a random access memory where it is utilized, for comparison with character identification codes for producing a printout label containing all the data for a particular patient. Each printout label also includes a patient's identifying number, the date the data was recorded and the time of recording. The printed data may then be assembled with a patient's record to provide a continuous sequence of data relating to his condition. The data is uniformly presented for easy interpretation and analysis. Yet another feature of the present invention is to provide a data printer responsive to acquired data stored in an acquisition unit by a comparison of a plurality of character identifying codes with the acquired data.

In accordance with one embodiment of the invention a medical data acquisition and storage system comprises a display for providing a visual presentation of medical data inputed to the system. Automatically acquired data may be accepted through at least one information input and this data is gated to the display for visual presentation thereof. In addition to accepting automatically acquired data, manually generated data may be gated to the display for a visual presentation. When found acceptable, data visually displayed is gated into storage means having multiple locations for storing in the data sequence. The sequence of operation is under the control of a state controller that establishes the priority for gating data to the display means for any of the input sources.

In another embodiment of the invention, a medical data acquisition and display system comprises a data printer and one or more acquisition units for acquiring and storing a quantity of medical data from one or more patients by at least one probe connected to the acquisition unit. The medical data in an acquisition unit is stored in a printer memory by transfer means that gates the data from one of the acquisition units to the memory. A display as part of the data printer includes multiple characters each identified by a particular identifying code; each of these identifying codes are compared with the stored medical data in the printer memory and a display signal is generated upon a predetermined comparison condition. The display signal actuates the display to cause a preselected character to be presented. The entire system is controlled by a central controller for sequentially advancing each identifying code and each entry of medical data for comparison.

Other features and advantages of the present invention will become more readily apparent from the following description along with the accompanying drawings and the appended claims.

Referring to the drawings.

Figure 2:
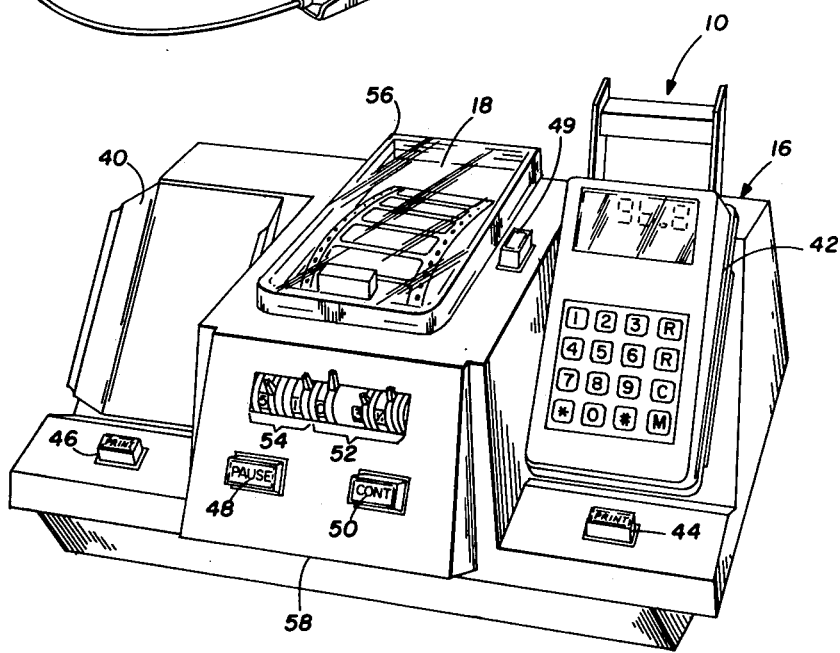
FIG. 2 is a pictorial view of a data printer responsive to acquired data in an acquisition unit for printing labels for individual patients setting forth the acquired data along with a patient's identification number, the date of entry and the time of entry.
Figure 3:
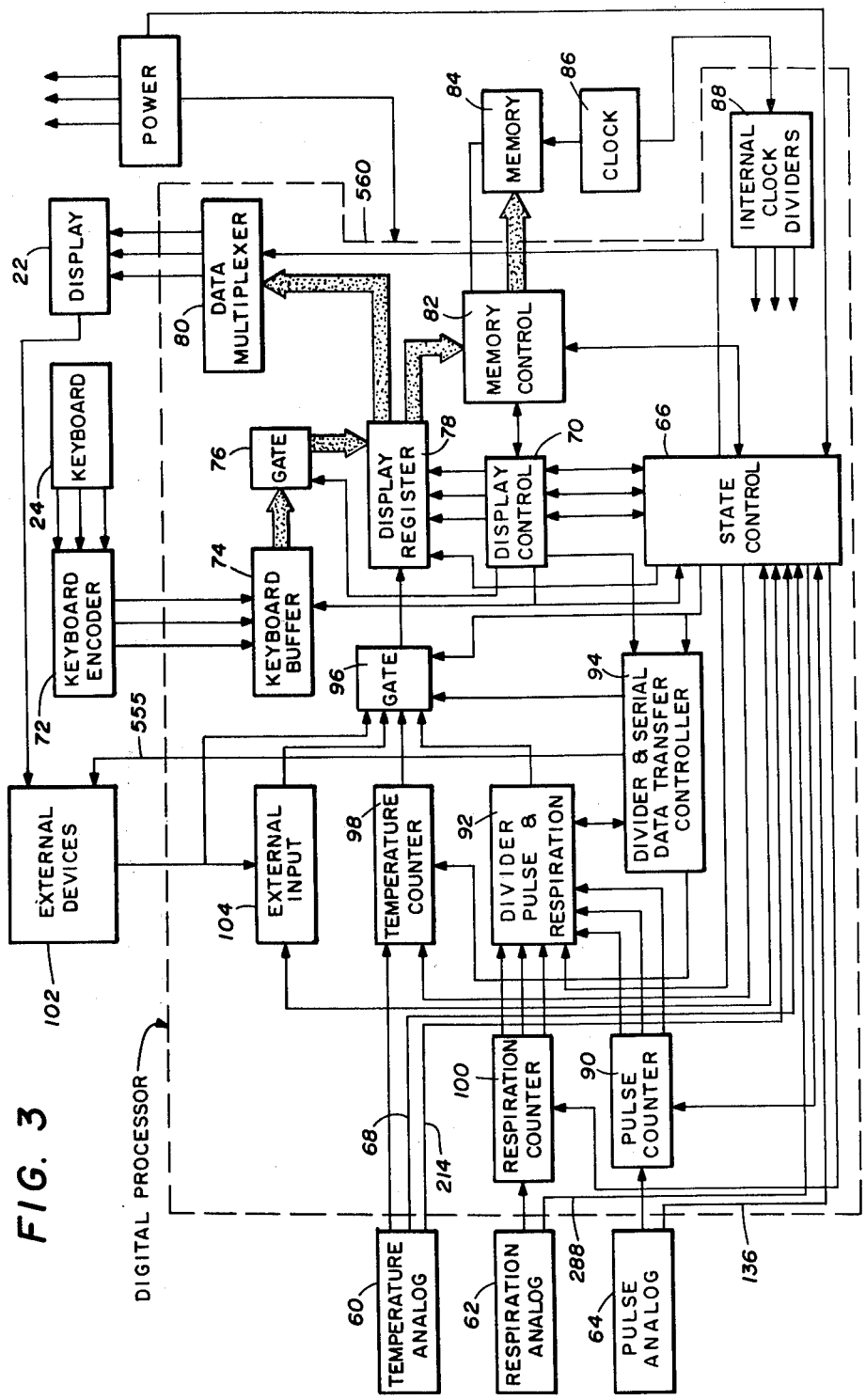
FIG. 3 is a block diagram of the data acquisition unit including analog-to-digital converters for temperature, respiration rate and pulse rate transducers.
Figure 6:
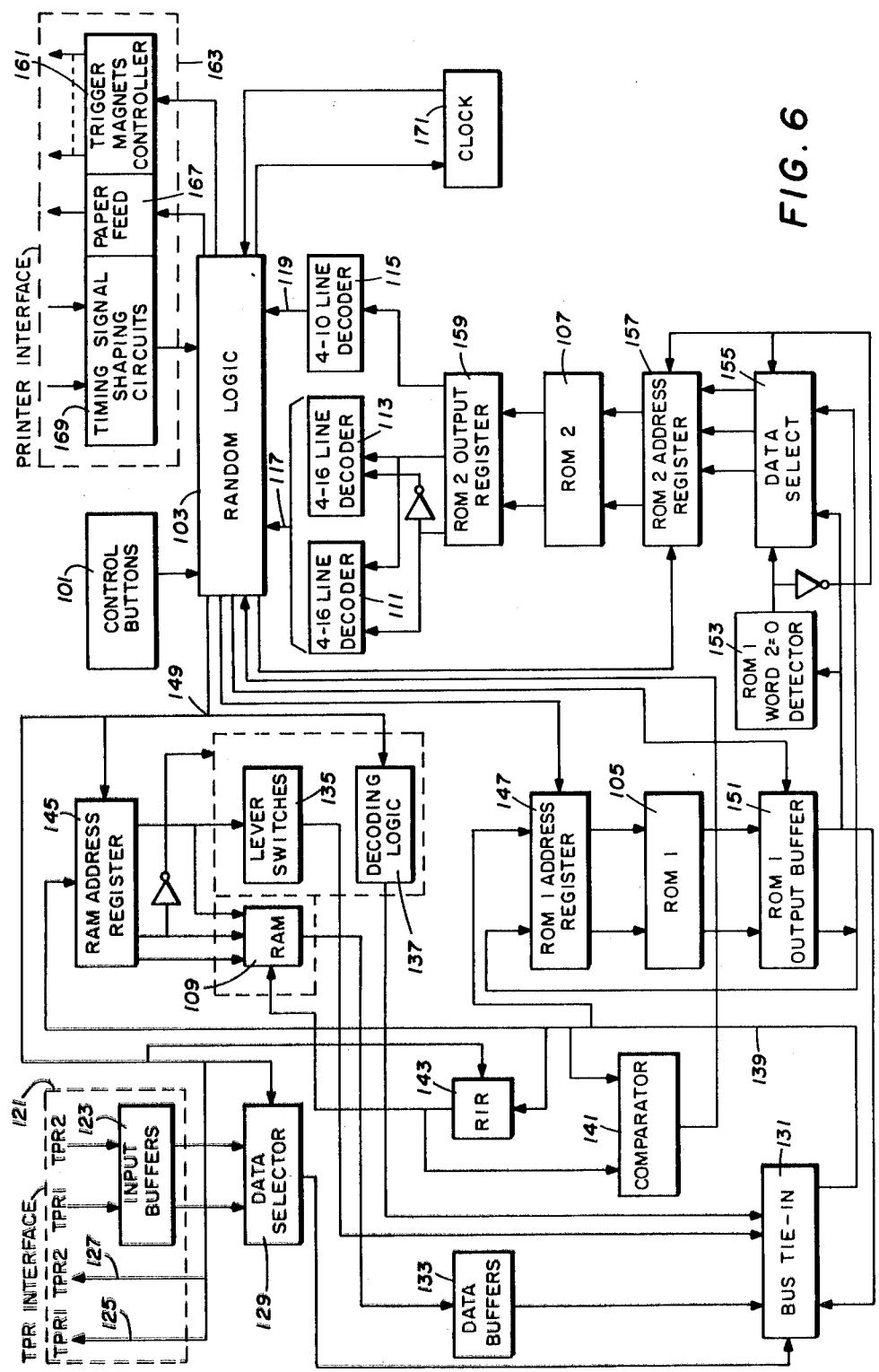
Figure 7A:
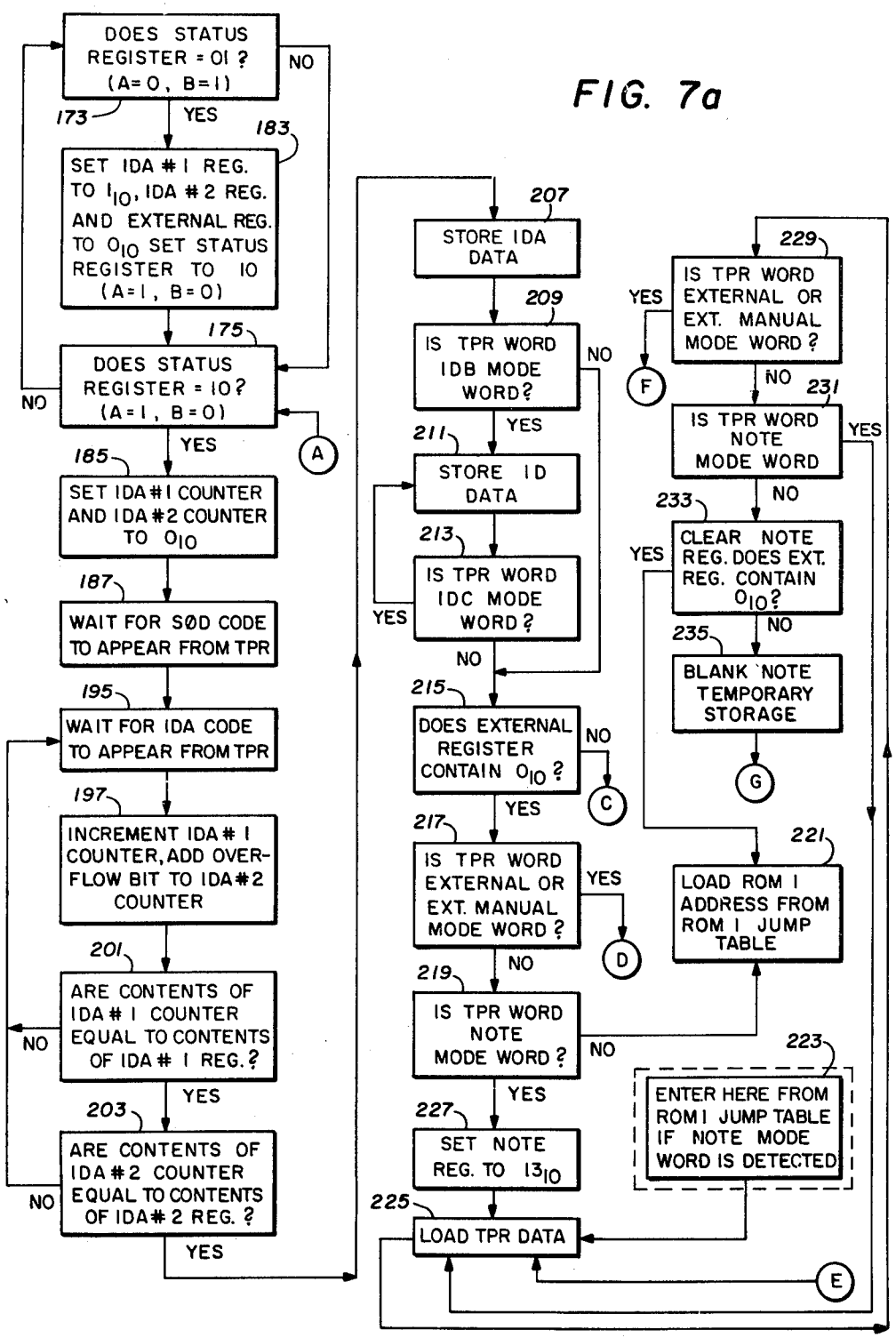
Figure 7B:
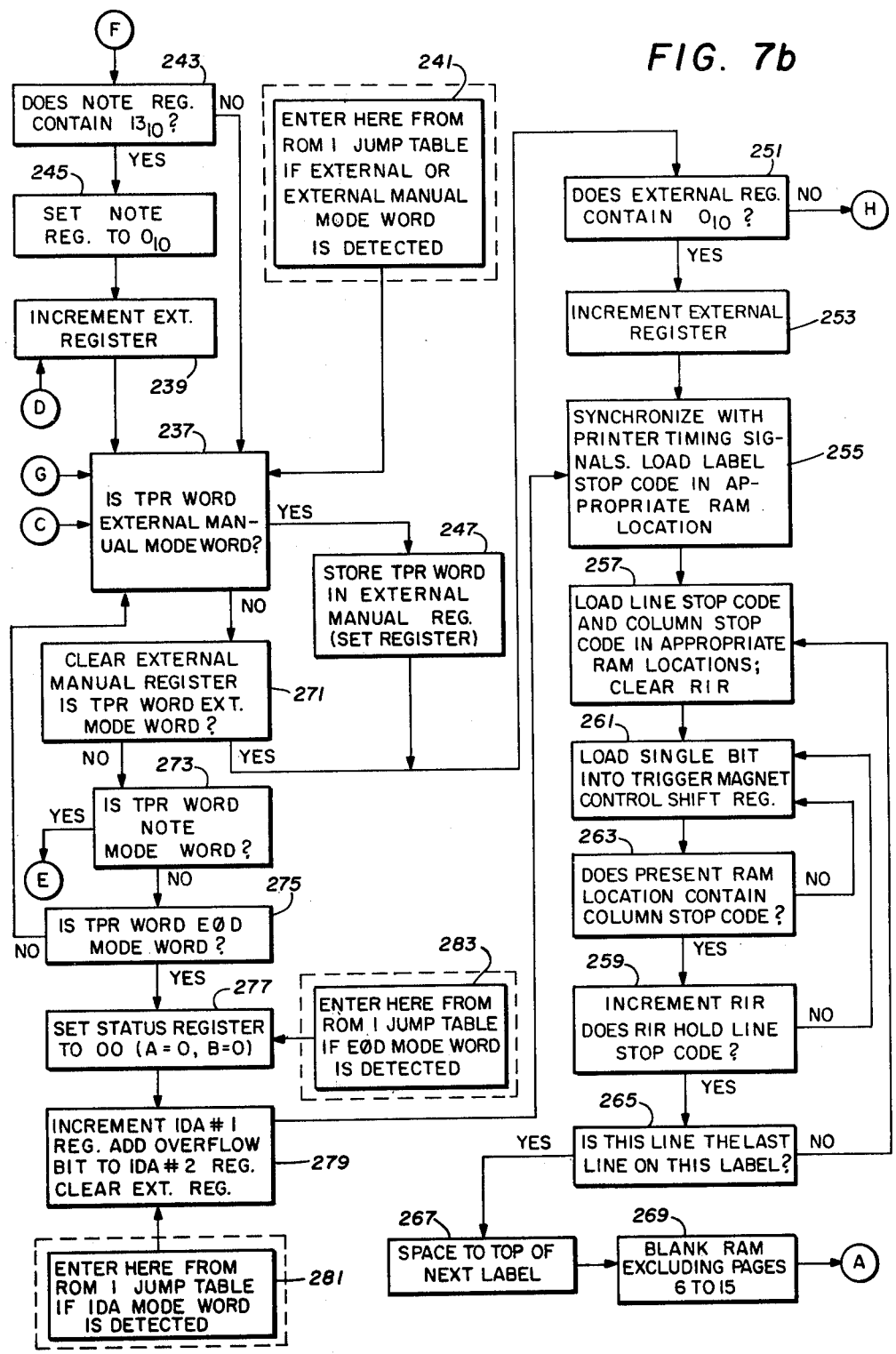
Figure 7C:
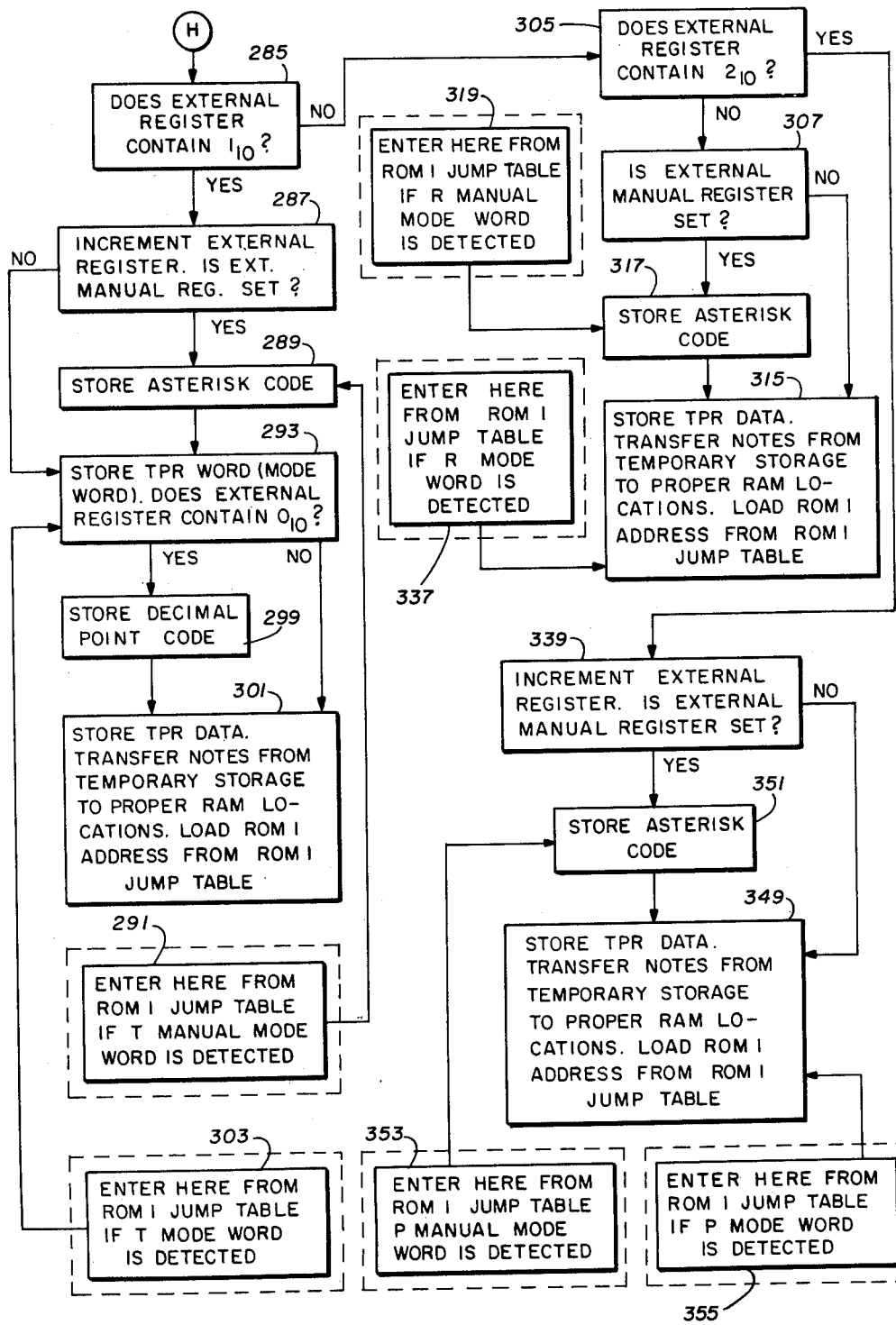

FIGS. 4a, 4b, 4c, 4d, and 4e comprise a schematic diagram for each of the blocks of FIG. 3 connected to the digital processor of FIG. 3;

FIGS. 5a, 5b, 5c, 5d, 5e, 5f, 5g, 5h, 5i, 5j, 5k, 5l and 5m comprise a logic diagram for the digital processor including various blocks within the dotted outline of FIG. 3;

FIG. 6 is a block diagram of the data printer of FIG. 2 for accepting stored data from an acquisition unit to be printed on labels with patient identification; and FIGS. 7a, 7b and 7c comprise a flow chart of the operation of the data printer for comparing each entry in an acquisition unit with a character identifying code for a label printing operation.

Figure 1:
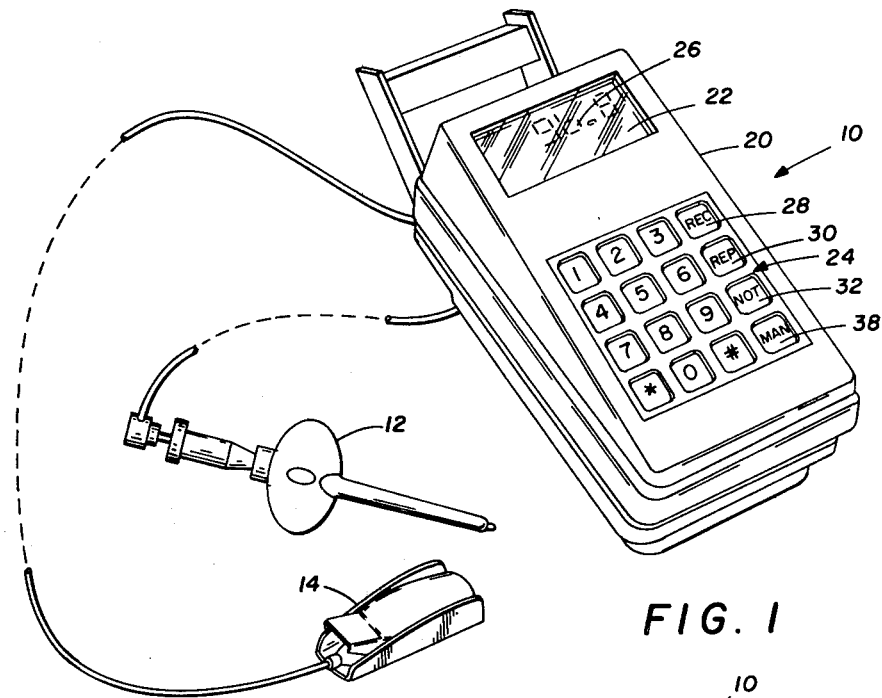
FIG. 1 is a pictorial view of a battery powered data acquisition unit with temperature, respiration rate and pulse rate transducers connected thereto.

Functionally, the system of the present invention can be divided into two component units or systems, the first is a data acquisition unit 10 or TPR unit as shown in FIG. 1. Specialized transducer probes 12 and 14 are utilized to measure a patient's vital signs such as temperature, pulse rate and respiration rate, and the acquisition unit converts this data into a digital format for storage in a circulating memory. The second unit is a data printer 16, as illustrated in FIG. 2, and functions in response to information previously recorded in the circulating memory of the acquisition unit 10 and producing hard copy patient labels 18.

Referring to FIG. 1, the data acquisition unit 10 includes a housing 20 having a window display 22 and an array of 16 keyboard switches 24. Typically, the display 22 provides a numerical readout 26 and other operating indicator lights as will be explained.

Coupled to the acquisition unit 10 is the temperature and respiration rate probe 12 generating an analog voltage varying with the patient's temperature and a second analog voltage with a frequency equal to the patient's respiration rate. The probe 12 may be of the type described and claimed in the copending application of Emmett L. Hudspeth et al, Ser. No. 346,952. Also coupled to the data acquisition unit 10 is the pulse rate probe 14 of the type commercially available to produce an analog voltage with a frequency related to the patient's pulse rate. In one form of a pulse probe 14, the probe comprises a clothespin-like clamp that fits over a patient's finger and includes a light source and light sensor. The light source illuminates the patient's fingertip and the light sensor responds to the light transmitted through the fingertip which varies with a frequency related to the patient's pulse rate. The volume of blood in a patient's finger changes the absorption of light from the source causing the light impinging on the sensor to change as a function of the amount of blood in the patient's fingertip, which in turn varies with his pulse.

Considering the keyboard switches 24, there are four control switches for operator use. These are labeled RECORD, REPEAT, NOTE and MANUAL START (all abbreviated in the FIGURE). The RECORD switch 28 is operator actuated to transfer data being displayed in the numerical readout 26 into the circulating memory of the acquisition unit and is active and effective any time there is numerical information being presented in the readout.

If the data visible in the display window 22 is unsatisfactory for any reason, an operator actuates the REPEAT switch 30 to clear the display for accepting new data, either automatically acquired or manually entered from the keyboard switches. In the case of temperature, pulse rate, or respiration rate, this causes a resampling of the analog voltage produced by the probe, either probe 12 or probe 14. The variable, either temperature, pulse rate or respiration rate, is recalculated and the newly calculated value presented at the numerical readout 26. This new data can then be transferred into the internal memory by actuating the RECORD switch 28 or the system can again calculate a new data value by again actuating the REPEAT switch 30. The REPEAT swith 30 is enabled any time the unit 10 is showing a number in the numerical readout 26.

The NOTE switch 32 may be used whenever the unit is accepting data either from the probes 12 or 14 or other transducers. If data is currently being presented, but has yet to be recorded in the circulating memory, actuating the NOTE switch 32 causes the display to be cleared. Meanwhile, the unit is transferred to the note mode. At this point, the operator may manually enter, by means of the numerical switches, coded notes to provide additional information about the patient. For example, a pre-establised code number represents weakened or irregular pulse. This code number may be recorded in the circulating memory by actuating the RECORD switch 28 after the operator has entered the code number when in the note mode. In addition, this note mode can be used to record relatively unrelated data such as a patient's status, blood pressure, diet or medications. After recording a coded note, the acquisition unit returns to its previous mode.

The acquisition unit 10 is normally activated automatically by the rise of the temperature at the probe 12 above 90° F. In special situations where the temperature portion of the probe 12 is not connected to the unit 10 or where the ambient temperature is always above 90° F., then the unit 10 can be activated by actuating the MANUAL START switch 38. This advances the unit to the identification mode and permits normal operation without requiring that temperature data be taken.

The acquisition unit 10 is provided with a four digit numerical readout 26, which is capable of displaying numbers from 0–9999, and in addition there are also five function indicators representing an identification (ID) mode, a temperature (T) mode, a pulse rate (P) mode, a respiration rate (R) mode, and an external (E) mode. When the unit 10 is functioning in each of the various modes, the appropriate function indicator will be illuminated with the NOTE mode indicated by the periodic flashing of any function indicator.

The ID mode indicator is illuminated when the unit 10 is in the identification mode and serves to inform an operator that the unit is ready to accept numerical data pertaining to a particular patient's identification. When in the temperature mode, an indicator is illuminated to again identify to a user that the unit is ready to accept temperature related data. Similarly, in the pulse mode the pulse mode indicator is illuminated and in the respiration mode the respiration mode indicator is illuminated to indicate that the unit is ready to accept pulse and respiration related data, respectively. When the unit is accepting external data, other than from the probes 12 and 14, the external indicator is illuminated indicating that the unit is in a mode for accepting such externally generated data. Actuating the RECORD switch 28 when data is present in the display always takes the unit 10 out of a previous mode and causes the operation sequence to advance to another sequencing mode.

Returning to the numerical keyboard, it comprises switches identified by 0–9 for the manual entry of data for presentation at the readout 26 including patient identification data. The numerical keyboard also allows the manual entry of data from patients who are too ill to accept the probes 12 and 14. In addition, the keyboard switches are also used whenever the numerical readout 26 is blanked and waiting for an identification code to be entered. The numerical switches are also actively coupled to the system when there is data presented in the numerical readout and actuating the numerical switches will modify the displayed data. To manually override data presented in the readout 26, the appropriate numbered switches are actuated and this data overrides that in the display. When the first digit from the keyboard is entered, the complete data entry presented at the readout 26 is erased, and the corresponding number is displayed in the least significant position of the display. Each time a succeeding numerical switch is actuated, the corresponding number is displayed in the least significant position and all previously entered numbers are shifted one place to the left. Each time a number is entered, the number in the most significant position of the readout is lost. Data that has been manually entered via the keyboard switches is especially coded internally and this special code is stored in the internal memory to later denote manual entries when the data is printed.

In normal operation, the unit 10 will be utilized when making "rounds" in a hospital nursing unit. Here the nurse or health-care attendant will go from bed to bed and acquire data relating to the temperature, pulse rate and respiration rate from each patient in the unit. This data, once acquired, is stored in the internal memory of the unit 10 for further hard copy printout by the printer 16.

Referring to FIG. 2, after a nurse or health-care attendant has made a round, or after the circulating memory of the acquisition unit 10 is completely loaded, the unit 10 is placed in one of two chutes 40 or 42 of the printer 16. The printer is equipped to accept two acquisition units 10 at one time, although the printer will address the units one at a time to make a permanent recording of the data stored therein. Assuming that the unit 10 has been inserted into the chute 42, the contents of the memory of the acquisition unit is printed on the labels 18 by pushing a print button 44. A similar print button 46 is provided for the chut 40 and is activated to address an acquisition unit in the chute 40 for printing out the data there in on the labels 18. Once the print button for one position has been actuated, the data stored in the respective acquisition unit must be completely printed, or the unit removed from the chute, before data stored in the second acquisition unit in the opposite chute can be printed.

There are three additional controls on the printer, these are a PAUSE push-button 48, a CONTINUE push-button 50 and a PAPER FEED push-button 49. The PAUSE push-button 48 advances the printer operation to enter a stop loop when it has completed printing the data for the present label. This control is provided to be utilized if the printer runs out of labels 18, if the feed mechanism for the labels becomes jammed, or for any other reason requiring a temporary shut down of the printer. Printing may then be resumed by actuating the CONTINUE push-button 50 whereby the printer sequence takes up printing with the data in the acquisition unit 10 which follows the data last printed. Alternatively, printing may be resumed by actuating a second time the print button, in which case the printer sequence resumes printing with the first data stored in the acquisition unit 10. The PAPER FEED push-button 49 is actuated to cause labels 18 to be advanced one line at a time for the purpose of loading or alignment.

In addition to the push-button controls, the printer 16 is also provided with date switches 52 for setting in a date to be printed on the labels 18; there are also provided time switches 54 for setting in the time of the recording. This time data is also printed on the labels 18 and includes the time of day and a notation of a.m. or p.m.

The printer mechanism itself (not shown) is a type referred to as a flying printer wherein a print drum rotates continuously. The printing mechanism is located below the transparent cover 56 in the print housing 58. Printing is carried out by selecting a print hammer corresponding to a character disposed on the surface of the drum. In conventional large capacity flying printers, the print hammers are generally electrically driven but other driving techniques are possible.

The printer mechanism, per se, utilized in the present system is of conventional design responding to signals generated within the printer 16. The printer mechanism sends three signals to the control circuit of the unit 16, these are denoted as the printer reset signal, the TP and TL signals. A reset signal occurs once for each complete revolution of the print drum and the TP and TL signals occur for each row of characters on the print drum. The TP signal occurs prior to the row of characters passing under a print hammer and the TL signal occurs at the completion of a row of characters. Selection of a character to be printed is accomplished by comparing a character identifying code with the data transferred from the acquisition unit 10. This will be explained in greater detail.

Referring to FIG. 3, there is shown a block diagram of the acquisition unit 10 including a temperature analog circuit 60 and a respiration analog circuit 62, both of which may contain part of the probe 12 and a pulse analog circuit 64 which may contain the probe 14. Each of the analog circuits 60, 62 and 64 connects to other circuitry within the housing 20 wherein the analog signals are converted to binary coded decimal (BCD)

Within the housing 20 of the acquisition unit 10, there is included a state controller 66 comprising logic for sequencing the unit through various operational modes. Initially, the state controller 66 determines whether the probe portions of analog circuits 60, 62 and 64 are connected to the system. In addition, the state controller 66 responds to a signal from the temperature analog circuit 60 to initiate operation of the acquisition unit.

As mentioned, the acquisition unit is enabled in an automatic mode when the temperature sensor in the probe 12 reaches 90° F. This temperature signal is coupled to the state controller 66 over a line 68 from the analog circuit 60. After the circuit has been enabled in the automatic mode from the temperature analog circuit 60, the state controller 66 generates a code to a data multiplexer 80 to initiate the illumination of an ID mode indicator in the display 22. The system is now in the ID mode and an operator enters a patient's ID through the keyboard switches 24. Actuating the switches 24 generates signals to a keyboard encoder 72 that converts the closing of a switch into a binary code to a keyboard buffer 74. Coded ID data in the buffer 74 is gated through a gate 76 to a display register 78 which is enabled by the display control 70 to transfer ID data through the data multiplexer 80 to the display 22. The operator upon verifying that the numerical readout 26 of the display 22 accurately shows the patient's ID number, actuates the RECORD switch 28 and data from the register 78 is transferred through a memory control 82 to a memory 84.

The heart of the acquisition unit 10 is the solid state memory 84 in which the stored data is continually recirculated around a memory loop at an established rate. Typically, the memory 84 is composed of twelve 512-bit P-channel MOS dynamic shift registers circulated at 16 KHz bit rate. The circulating frequency to the memory 84 is generated in a clock 86 that also provides clock pulses to a clock divider 88 to generate internal clock pulses to various sections of the unit.

Thus, to initiate operation of the acquisition unit 10, the probe 12 is placed in the patient's mouth, and the increase in temperature through the temperature level of 90° F. causes the unit to turn on the ID mode indicator in the display 22 and initiate acquisition of data from the three analog circuits 60, 62 and 64. The operator now enters the patient's ID number by using the keyboard 24. When one of the numeric keys is actuated, the corresponding number is coded in BCD and stored in the keyboard buffer 74; it is then shifted into the display register 78 and displayed in the first numerical readout in the display 22. Up to three additional ID digits may then be entered through the keyboard 24 to the display register 78. After the correct ID number is presented in the display 22, it is stored in the memory 84 by actuating the RECORD switch 28. The acquisition unit 10 may be programmed to accept patient ID numbers with more than four digits. This will be explained in greater detail.

When the RECORD switch 28 is actuated, the state controller 66 automatically steps to the next function, which is the pulse mode. The state controller 66 again generates the proper binary code, which turns on the P mode indicator in the display 22. The pulse rate analog circuit 64 generates an output signal having a repetition rate the same as the frequency of the patient's pulse rate as sensed by the probe 14. This pulse rate signal is connected to a pulse rate counter 90 that responds to the signal generated by the pulse analog circuit 64.

Initially, the counter 90, which in effect is two registers in tandem, was reset by the state controller 66 in the idle mode. Thereafter, for each pulse rate signal from the analog circuit 64, the first register advances one count and between the time when it has received four pulses and the time when it has received twelve pulses it generates an enable signal to the second register of the pulse rate counter 90. A window in time is generated which is proportional to the average period of the patient's pulse and is in fact eight times the patient's average pulse period. During this length of time, between the fourth and twelfth pulses from the analog circuit 64, a clock from the divider 88 is counted in the second register such that the count in this second register is inversely proportional to the pulse rate of a patient.

An output from the second register of the pulse rate counter 90 is transferred to a divider network 92 that consists of a digital divider that uses as a numerator one of two numbers hard wired into the circuit. The denominator for the divider network 92 is the count in the second register of the counter 90. The numerator hard wired into the divider is selected to scale the clock pulse count in the second register such that after completing the division process, the divider network 92 contains the patient's average pulse rate in pulses per minute.

The divider network 92 is controlled by the output of a data transfer controller 94 which in turn is sequenced from the display controller 70 and the state controller 66. The pulse rate, in pulses per minute, in the divider 92 is a binary code that is transferred through a gate 96 to the display register 78 in response to a transfer signal from the controller 94. This transfer takes place after the divider network 92 has completed the division process.

In one embodiment of the invention, the temperature, pulse rate and respiration rate circuits all generate pure binary coded information. Prior to displaying such information in the display register 78, logic circuitry, to be detailed, provides a serial binary to BCD (Binary Coded Decimal) conversion which results in the BCD data being stored in the display register at the completion of the transfer of data thereto. Data entered through the keyboard buffer or through external inputs, however, is supplied in BCD form and the display register 78 passively accepts this data with no conversion process.

The pulse rate code in the display register 78 is transferred through the data multiplexer 80 and displayed in the numerical readout 26 of the display 22. If the operator is satisfied that the number in the display 22 accurately reflects the patient's pulse rate condition, the RECORD switch 28 is actuated and the data in the display register 78 is transferred through the memory controller 82 to the memory 84.

If the data presented in the display 22 does not satisfy the operator that it represents a true indication of the patient's pulse rate, there are two alternatives available. One, the operator actuates the REPEAT switch 30 which sets the state controller 66 to reset both registers of the pulse rate counter 90 and the divider and serial transfer controller 94 so that a new pulse rate measurement is made and transferred to the display register 78. In the alternative, the operator may enter, through the numerical keyboard, a manual pulse rate measurement. This data is then stored in the memory 84 by actuating the RECORD switch 28. When manually generated data is stored in the memory 84, the memory controller 82 produces a binary code highlighting the memory entry to signify that it was manually generated data.

Under normal operating conditions the state controller 66 advances the operating sequence from an idle mode to an identification mode, from the identification mode to the pulse rate mode, from the pulse mode to the temperature mode and from the temperature mode to the respiration rate mode. When the operator actuates the RECORD switch 28 to transfer the data in the display register 78 through the memory control 82 to the memory 84, the display control 70 generates a signal to the state controller 66 to advance the sequence to the next mode.

After recording the pulse rate data in the memory 84, the state controller 66 advances the system to the temperature mode. In the temperature mode, a frequency signal from the temperature analog circuit 60 is transferred to a temperature counter 98 in response to a control signal from the state controller 66. At the appropriate time in the acquisition cycle of the temperature mode, the cycles of the frequency signal from the circuit 60 are counted for a fixed period of time in the temperature counter 98 which has been preset with a count representing 90° F. This results in a total in the counter 98 that is a function of the frequency of the circuit 60 and hence is a function of temperature. In effect, the counter 98 counts a variable incoming frequency for a fixed period of time such that by presetting the counter to 90° F. and starting the counter at a fixed time and stopping it at a fixed time later there is generated a count that is a direct function of temperature. Typically, the counter is enabled for 166 milliseconds and this results in the counter being incremented one count for each 0.1° F. that the temperature probe is above 90° F.

In the temperature mode, the system has a capability of measuring temperature by a direct count or by a predictive algorithm count. Normally, the predictive algorithm sequence is utilized as it produces a temperature reading in a shorter elapsed time period. In the direct reading sequence, the total in the counter 98 represents the actual temperature of the probe 12 at the time the temperature measurement is made. Unless the probe 12 is left in the patient's mouth sufficiently long to stabilize at the patient's temperature there results a measurement which may differ from the patient's true temperature. For this reason, the direct count mode is normally used only when adequate time has been allowed to permit thermal equilibrium between the probe 12 and the patient's mouth.

In the predictive algorithm sequence, a measurement is achieved in the counter 98 before the probe reaches equilibrium. When the temperature of the probe passes through 90° F., the counter 98 is enabled for a predetermined fixed length of time after a constant has been added to give a total reading representative of a patient's temperature before the probe is actually stabilized. Essentially, there is a prediction of what the temperature will be when the probe has stabilized. In implementation of this addition of a constant, after the probe has passed through 90° F., a fixed delay is initiated and the frequency from the circuit 60 is counted in the counter 98 for the fixed time period after this delay. In effect, the counter is started 1° higher than 90° F., that is, 91° F., which accomplishes the addition of the constant.

As mentioned previously, an operator has the option of repeating a measurement if that presented in the numerical readout 26 appears to be an erroneous measurement. When the operator actuates the REPEAT switch 30, the temperature counter 98 bypasses the predictive algorithm sequence and uses the direct reading sequence. Also, when the acquisition routine is initiated by actuating the MANUAL START switch 38, the temperature counter again bypasses the predictive algorithm sequence and uses the direct reading sequence for temperature measurement. In the direct reading sequence, the frequency signal coupled to the counter 98 is counted for a fixed period of time thereby giving a measure of a patient's temperature. Again, the counter starts at a base count of 90° F. and adds one count for each one tenth of a degree of temperature above this initiating level. The operator uses the REPEAT switch 30 to repeat the temperature measurement and may determine when thermal equilibrium of the probe 12 is achieved by comparing successive measurements as shown in the numerical readout 26.

Summarizing the two temperature acquisition sequences, the predictive algorithm sequence is started when the temperature of the probe 12 rises above 90° F. After a predetermined delay time, the counter 98 is preset to a count of 91° F. and then actuated for a fixed period of time. The resultant count in the counter 98 is 1° F. higher than the temperature of the probe 12 and represents a prediction of the temperature the probe 12 would achieve if permitted to attain thermal equilibrium with the patient's mouth. The direct reading sequence is started when the operator presses the MANUAL START switch 38. It is also started any time a temperature measurement is repeated by actuating the REPEAT switch 30. Without delay the counter 98 is preset to a count of 90° F. and activated for a fixed time period. The count stored in the counter 98 reflects the actual temperature of the probe 12. The operator must determine whether the probe 12 has reached thermal equilibrium with the patient's mouth.

At an appropriate time after actuating the counter 98, the binary data stored therein is transferred through the gate 96 to the display register 78. During the transfer the data is converted to BCD by the display register 78. Data in the display register 78, as explained, is transferred through the data multiplexer 80 to the display 22. If the operator is satisfied with the data displayed, the RECORD switch 28 is actuated to transfer the temperature data from the display register 78 through the memory control 82 to the memory 84. Again, a signal is generated to a state controller 66 to advance the sequence from the temperature mode to the respiration rate mode.

Measurement of the respiration rate is similar to the pulse rate measurement. The respiration rate sensor, as part of the probe 12, consists of a bead thermistor placed in the nasal airstream of a patient. Respiratory air flow induces temperature changes in the thermistor which are amplified and conditioned in the respiration analog circuit 62 to provide an analog frequency signal to a respiration rate counter 100. Thereafter the operation in the respiration mode is analogous to operation in the pulse mode.

The counter 100 registers pulses generated by the analog circuit 62 in a first register which is used to generate a window for enabling a second register receiving a clock from the divider 88. At the second count in the first register the second register is enabled and advances in accordance with the frequency from the divider 88 until the sixth count in the first register. The count in the second register is proportional to a period of the patient's respiration rate. Again, a scaling factor is present and the output of the respiration rate counter 100 is transferred to the divider 92 to produce a binary code equal to the patient's respiration rate. In accordance with control pulses from the controller 94, the respiration rate binary code is gated through the gate 96 to the display register 78. During the transfer the data is converted to BCD by the display register 78. Next, the data is displayed, and if found acceptable, transferred to the memory 84 by actuation of the RECORD switch 28.

At this time, under normal operating conditions of the acquisition unit 10, a particular patient's medical data is stored in the memory 84. The state controller 66 returns the system to an idle mode. The operator removes the probes 12 and 14 from the patient. The unit is now ready for the next patient.

In the previous description it was assumed that temperature, respiration rate and pulse rate data are taken from each patient. If any one of the three probes for these measurements are not attached to the unit, the state controller 66 skips over that measurement and advances the sequence to the next mode. Thus, the unit has the capability of measuring temperature pulse and respiration or any combination of the three. Any one or more of these three can be measured and the others automaticaly deleted from the measurement process if the probes are not attached.

In addition to temperature, respiration rate and pulse rate measurements, additional medical data may be gathered for a patient and stored in the memory 84. This additional data is gathered from devices identified in FIG. 3 by the block 102. Examples of such external devices include a blood pressure measuring transducer that will measure a patient's systolic and diastolic blood pressure and convert them into BCD data, serialize the data and send it on an input line to the display register 78. Data is shifted into the display register 78 through the gate 96 under the control of the controller 94 and the external input circuit 104. In addition to numerical data, an identifying character is also generated by the external device to identify the type of medical data. That is, data relating to a blood pressure measurement would be identified with an appropriate coded prefix such that when printed out on the label 18 the measurement is readily identifiable. This identifying character is also stored in the display register 78. The data is then presented in the display 22, and if found acceptable, shifted into the memory 84 by actuating the RECORD switch 28.

Another example of an external device is a transducer for measuring a patient's weight, such as in an outpatient clinic. Still another example of an external device is a drop counter that measures the patient's rate of intravenous infusion or urine output. Such a device is semi-permanently attached to the patient's bed and as the nurse or attendant measures the temperature, pulse and respiration of the patient, this external device is coupled to the unit for storing in the memory 84.

In the sequence of operation of the acquisition unit 10, after the state controller 66 has stepped the sequence to the respiration rate mode and the respiration rate data is transferred to the memory 84, the state controller checks to determine if any external devices are coupled to the external input circuit 104. If an external device is detected, a first pass at the external mode is made for transferring the BCD data generated by the external device to the memory 84. Note that the external device generates the BCD data and it is merely shifted through the system for display and storage in the memory 84.

As the operator actuates the RECORD switch 28 to transfer data from the first external device into the memory 84, the state controller 66 again cycles to the external mode to determine if a second such device is coupled to the external input circuit 104. If a second device is detected, the external mode is again repeated and the data stored in the memory 84. Again, the state controller 66 recycles to the external mode to evaulate if still a third device is coupled to the external input circuit 104. If a third device is detected, the sequence again cycles through this mode to transfer data to the memory 84. If at any time the state controller cycles to the external mode and an external device is not coupled to the circuit 104, then the sequence advances to the idle mode as mentioned previously.

As mentioned, the sequence of operation of the acquisition unit 10 is first the ID mode, next is the pulse mode, then the temperature mode, and a respiration mode. Following, there is an external device mode wherein data from externally connected devices is stored in the memory 84. The memory is a serial memory, shift register, that is initially loaded with a start-of-data (SOD) word and an end-of-data (EOD) word. The SOD word is unique and used to indicate the first word of recorded data in the memory 84. The EOD word is also unique and is used to indicate the last word of data in the memory at any particular time.

Whenever new data is transferred to the memory 84 it begins recording at the position where the EOD word has previously located. After completing the transfer of new data into the memory 84, the EOD word is again recorded following the last data entry. For example, in the ID mode, the ID data is stored in the memory 84 in the next position following the SOD word. After the ID data has been stored, the EOD word is written in the next available location. Next is the pulse mode and as the pulse data is transferred to the memory 84 it is first written over the EOD word at the end of the ID data and the new EOD word is written after the pulse data. Thus, after each new data entry into the memory 84 the last entry is a new EOD word.

Each item of patient data, whether it be ID number, temperature, pulse rate, respiration rate, notes, or data from external devices, is stored in the memory prefixed by a coded mode word to unambiguously label the data. These mode words identify the nature of each piece of data so that the printer 16 can sort and display them properly. Additionally, the first coded mode word associated with each patient's data is an ID mode word referred to as an IDA code. Like the EOD and SOD codes, the IDA code is a unique code specifically reserved for the purpose of facilitating later separation of the data by the printer.

Figure 4A:
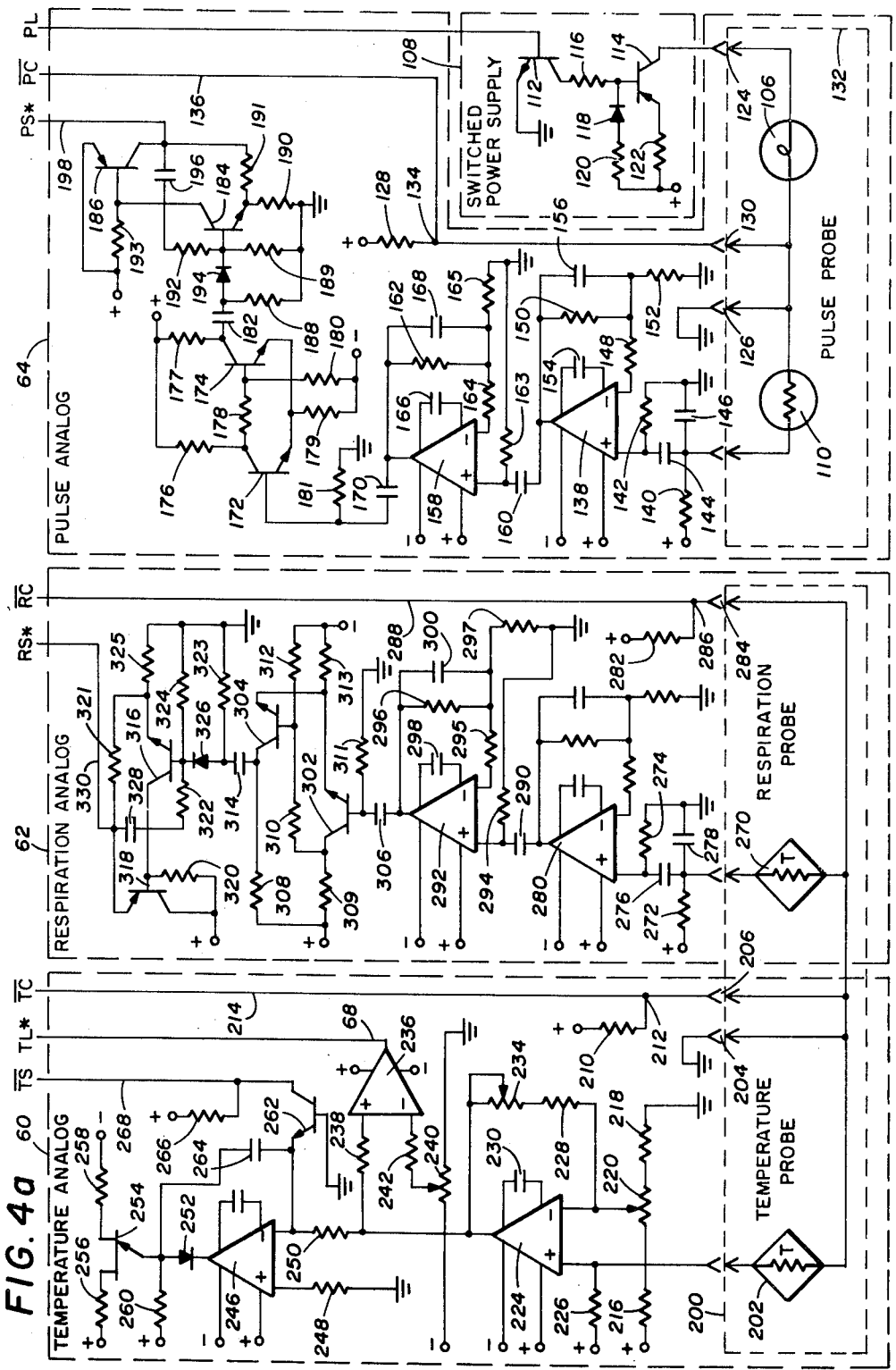

Referring to FIG. 4, and in particular to FIG. 4a, after the state controller 66 has received a signal indicating that the ID word has been written into the memory 84, it advances to the pulse mode wherein signals generated in the pulse analog circuit 64 are coupled to the pulse rate counter 90. The pulse rate probe includes a light source 106 coupled to a switched power supply 108 to illuminate a patient's finger to transmit light therethrough to a photocell 110. The volume of blood in the patient's finger changes the absorption of light, in the spectral region of sensitivity of the photocell 110, causing the resistance of the photocell to change as a function of the amount of blood in a patient's finger, which in turn changes with each heartbeat.

A logic signal for activating the switched power supply 108 is applied over a line PL to a transistor 112 having a collector coupled to a transistor 114 through a base drive resistor 116. Also part of the drive circuit for the transistor 114 is a diode 118 and resistors 120 and 122. A DC current in the collector of the transistor 114 is applied through a connector 124 to the light source 106.

Both the light source 106 and the photocell 110 are coupled to ground through a connector 126. Also connected to the interconnection of the source 106 and the photocell 110 is a probe present circuit comprising a resistor 128 connected to the positive terminal of a DC supply and through a connector 130 to the source 106 and photocell 110. Interconnecting the pulse probe 132 to the resistor 128 generates a logic signal at a terminal 134 that is transmitted over a line 136 to the state controller 66 as a signal that the pulse mode should be entered.

A change in resistance of the photocell 110 is converted into a varying voltage as an input to an amplifier 138. The resistance to voltage converter includes resistors 140 and 142 along with capacitors 144 and 146. A feedback circuit for the amplifier 138 consists of resistors 148, 150 and 152 along with capacitors 154 and 156. A voltage output from the amplifier 138 that varies with the resistance change of the photocell 110 is applied for further amplification to the input of an amplifier 158 through a coupling capacitor 160. Additional circuitry for the amplifier 158 includes resistors 162–165 and capacitors 166 and 168. An output of the amplifier 158 is coupled through a capacitor 170 to a Schmitt trigger comprising transistors 172 and 174. The Schmitt trigger also includes resistors 176–181.

Output pulses from the transistor 174 of the Schmitt trigger have a repetition rate that varies with the pulse rate as manifested by changes in resistance of the photocell 110. These voltage pulses are coupled through a capacitor 182 to a one-shot multivibrator comprising transistors 184 and 186. In addition to the transistors, the one-shot multivibrator consists of resistors 188–193, a diode 194 and a capacitor 196. Each pulse from the Schmitt trigger causes one output pulse to be generated by the one-shot multivibrator. The function of the one-shot multivibrator is to produce a series of uniform width voltage pulses having a repetition rate equal to a patient's pulse rate. These voltage pulses are transmitted over a line 198 to the pulse rate counter 90.

After writing the pulse rate data into the memory 84, the state controller 66 advances the acquisition unit 10 to the temperature mode wherein temperature related voltage pulses from the temperature analog circuit 60 are coupled to the temperature counter 98. As part of the temperature analog circuit 60 there is a temperature probe 200 comprising a thermistor 202 coupled to ground through a connector 204. Also connected to the thermistor 202 through a connector 206 is a circuit for sensing the presence of the probe 200. This circuit includes a resistor 210 connected to the positive terminal of a DC supply and generating a voltage at the terminal 212 when the probe is connected to the analog circuit 60. This voltage at the terminal 212 is a logic signal applied to the state controller 66 over a line 214. Whenever a voltage on the line 214 is present, the state controller 66 advances from the pulse rate mode to the temperature mode. Otherwise, the temperature mode is skipped and the state controller advances to the next mode.

Basically, the analog circuit 60 is a bridge amplifier where the thermistor 202 is part of a resistance bridge including resistors 216, 218 and 226, along with a variable resistor 220. An unbalance of the bridge caused by a variation in temperature at the thermistor 202 produces a voltage differential at the inputs of an amplifier 224. This unbalance voltage to the amplifier 224 is the difference between the temperature at the thermistor 202 and a bridge balance temperature as set by the variable resistor 220.

Also forming a part of the circuitry for the amplifier 224 is resistor 228 along with capacitor 230 and a gain potentiometer 234.

An output voltage from the amplifier 224 is applied to the input of a level sensor amplifier 236 through an input resistor 238. A second input to the amplifier 236 is generated at the wiper arm of a potentiometer 240 and coupled to the amplifier through a resistor 242.

The potentiometer 240 is set at the desired turn-on temperature of 90° F. and whenever the output of the amplifier 224 exceeds the voltage at the wiper arm of the potentiometer 240 the amplifier 236 generates a voltage output on a line 68 to the state controller 66. It is the voltage signal on the line 68 that turns on the acquisition unit to cause the state controller 66 to advance from the idle mode to the ID mode.

Also coupled to the output of the amplifier 224 is an amplifier 246 as part of a unijunction transistor oscillator to convert the voltage output of the amplifier 224 into a frequency signal. The amplifier 246 is differentially connected with one input coupled to ground through a resistor 248 and the second input connected to the amplifier 224 through a resistor 250. The output voltage from the amplifier 246 is coupled through a biased diode 252 to a unijunction transistor 254 having base one and two terminals connected through resistor 256 and 258 to DC supplies. The unijunction transistor oscillator is of a conventional design and includes a bias resistor 260 coupled to a DC supply and also to the timing capacitor 264. Amplifier 246 linearizes the charging of timing capacitor 264 and controls the charging current of the timing capacitor 264 in response to changes in the voltage output of amplifier 224. Additional components for the oscillator are output transistor 262 and its bias supply resistor 266. A frequency varying with the temperature at the thermistor 202 is generated at the collector of the transistor 262 in response to the oscillator signal applied at its emitter and is applied over a line 268 to the temperature counter 98.

As explained, after the temperature data has been stored in the memory 84, the state controller 66 advances the acquisition unit 10 to the respiration mode wherein signals generated at the respiration analog circuit 62 are coupled to the respiration rate counter 100. The analog circuit 62 includes a thermistor 270, as part of the temperature probe 200, that senses the rise and fall in the temperature of air passing over it. The patient exhales warm air which flows past the thermistor 270 and inhales cool air which is pulled back across the thermistor. This causes a cycling variation in the resistance of the thermistor 270.

This variation in resistance of the thermistor 270 is converted into a varying voltage by a circuit including resistors 272 and 274 along with capacitors 276 and 278. The voltage is then applied to an amplifier 280 having a feedback network including components similar in connection to those for the amplifier 13 of the pulse analog circuit 64.

Basically, the respiration analog circuit 62 is similar to the pulse analog circuit 64. As such, it is provided with a probe sensing resistor 282 connected to the thermistor 270 through a connector 284 and thence coupled to ground through connector 204. A voltage generated at the terminal 286 indicates that the probe is coupled to the system and a voltage on the line 288 is applied to the state controller 66 as an instruction for the controller to sequence to the respiration rate mode.

An output of the amplifier 280 is coupled through a capacitor 290 to one input of a differential amplifier 292 having associated circuitry including resistors 294–297 and capacitors 298 and 300. From the amplifier 292, a voltage varying with the resistance of the thermistor 270 is coupled to a Schmitt trigger comprising transistors 302 and 304 and circuitry therefor. The output of the amplifier 292 is coupled to the transistor 302 through a capacitor 306. Also associated with the transistors 302 and 304 are resistors 308–313.

The Schmitt trigger functions as a pulse forming circuit responsive to the output of the amplifier 292. Pulses from the Schmitt trigger generated at the collector of the transistor 304 are coupled through a capacitor 314 to a one-shot multivibrator consisting of transistors 316 and 318. Bias voltages for the transistors 316 and 318 are set by various resistor networks including resistors 320–325. Also associated with the one-shot multivibrator is a diode 326 and a capacitor 328. Uniform width voltage pulses are generated on a line 330 having a repetition rate equal to the respiration rate and coupled to the respiration rate counter 100 for storage in the memory 84.

Figure 4B:
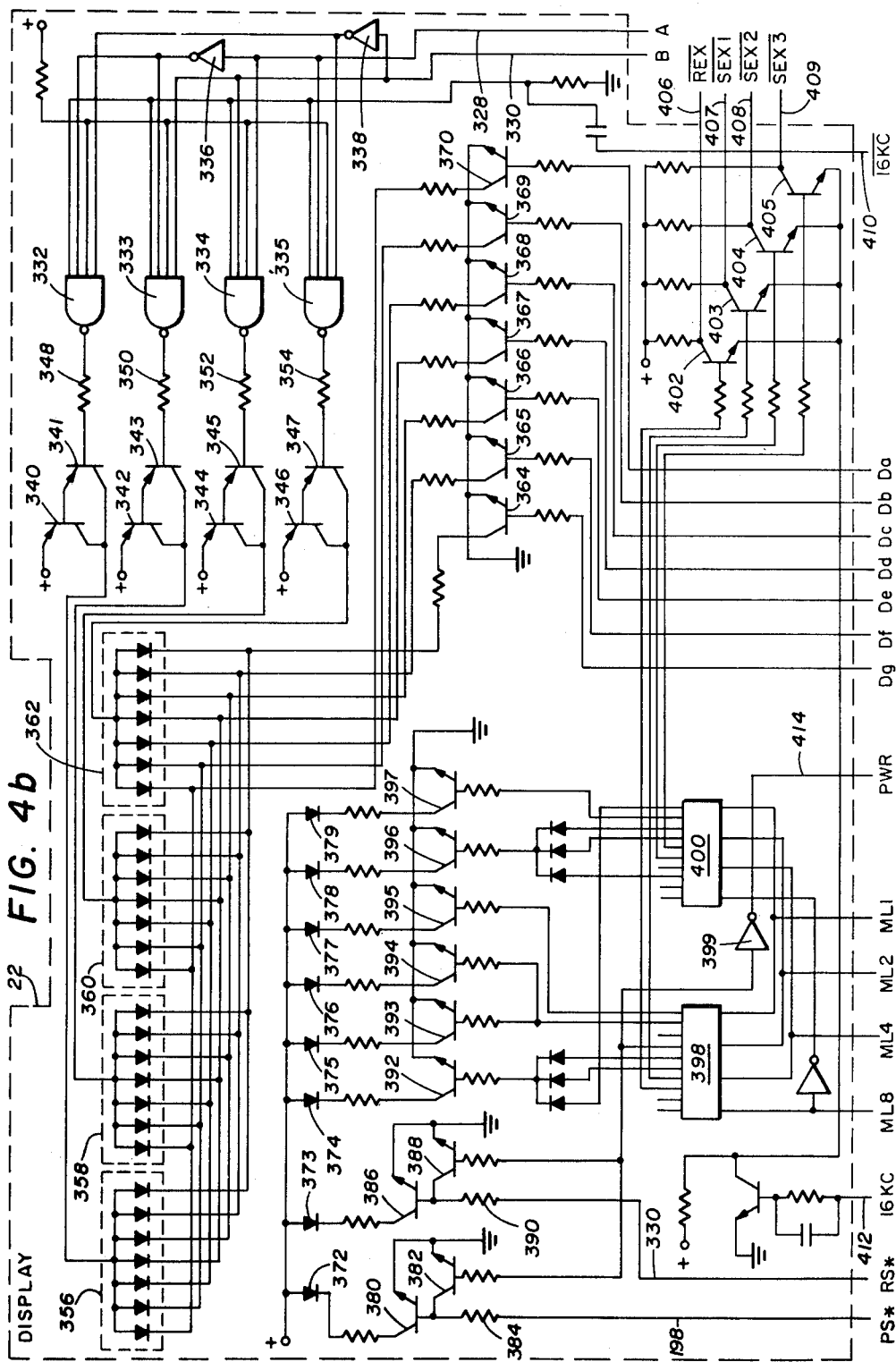

Referring to FIG. 4b, data generated by the circuits 60, 62 and 64 is gated through the gate 96 into the display register 78 and through a data multiplexer 80 to the display 22 over lines Da–Dg. In addition, control signals are coupled through the register 78 on lines 328 and 329. Control signals on the lines 328 and 329 are decoded in logic including NAND gates 332–335 and inverting amplifiers 336 and 338.

Decoded control signals from the NAND gates 332–335 are applied to a switching network consisting of transistors 340–347. Specifically, NAND gate 332 drives the switching transistor 341 through a resistor 348, the NAND gate 333 drives the switching transistor 343 through a resistor 350, the NAND gate 334 drives the switching transistor 345 through a resistor 352 and the NAND gate 355 drives the switching transistor 347 through a resistor 354.

Each of the switching transistor pairs drives one array of light emitting diodes (LEDs) as part of the display 22. Transistors 340 and 341 drive a diode array 356, the transistor pair 342 and 343 drives a diode array 358, the transistor pair 344 and 345 drives a diode array 360 and the transistor pair 346 and 347 drives a diode array 362. The individual diodes of each array are interconnected and coupled to control transistors 364–370 which in turn are individually connected to one of the data lines Da–Dg.

Operationally, control signals on the lines 328 and 329 along with data signals on the lines Da–Dg set the various transistor switches to illuminate the LED arrays 356, 358, 360 and 362 to present a numerical display in the display 22.

In addition to displaying data, there is also presented in the display 22 mode indicators comprising LEDs 372–379. The LED 372 is an indicator for the pulse rate signals generated on the line 198 of the circuit 64. This diode is controlled by switching transistors 380 and 382 interconnected through a resistor 384 to the line 198. The LED 373 is an indicator for respiration rate signals as generated on the line 330 of the circuit 62 and is controlled by switching transistors 386 and 388 interconnected through a resistor 390 to the line 330. The array of LEDs 374–379 are mode indicators and each is respectively controlled by a switching transistor 392–397. Each of the switching transistors is connected to the output of decoders 398 and 400 interconnected to control lines ML1, ML2, ML4 and ML8.

The operating mode of the acquisition unit is controlled by the state controller 66 and indicated by illuminating one of the LEDs 374–379. These diodes are controlled by coded data generated in the data multiplexer 80. This coded data is coupled to the decoders 398 and 400 where it is decoded to energize the correct LED.

In addition to controlling the LEDs 374–379, the output of the decoders 398 and 400 is also coupled to transistors 402–405 and inverter 399 as part of a selection network for external devices 102 coupled to the acquisition unit. These control signals to the external devices 102 are generated on the lines 406–409 and 414.

Also supplied to the display 22 are clock pulses on lines 410 and 412. The clock pulses are utilized to strobe the light emitting diodes such that they are energized for only a brief period. Typically, the clock pulses strobe the light emitting diodes such that they have about a 5% duty cycle during which time they are illuminated very brightly and the effect is that they appear to be of average brightness continuously.

Figure 4C:
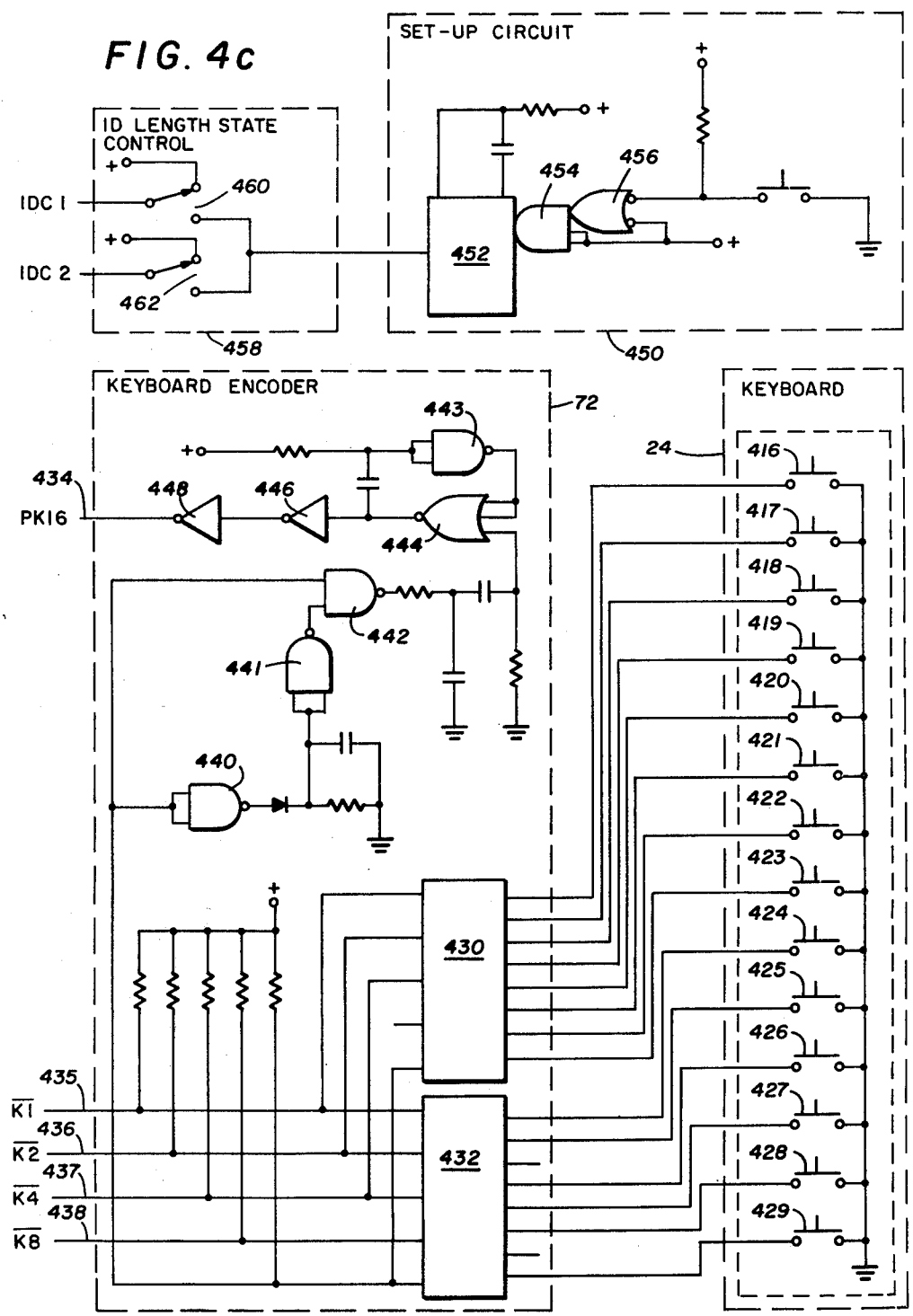

Referring to FIG. 4c, data in the register 78, as presented in the display 22, is transferred to the memory 84 in response to a command from the keyboard 24. The keyboard 24 comprises an array of momentary contact switches 416–429 each having a common connection to ground. Actuating any one of the keyboard switches provides a voltage to either encoder 430 or encoder 432. The encoders 430 and 432 are part of the keyboard encoder 72 and function to convert the voltage signal generated by actuating one of the key switches into a binary code on the output lines 434–438. Also forming part of the encoder 72 and associated with the line 434 is logic including NAND gates 440–443, and NOR gate 444 and inverting amplifiers 446 and 448. An output code on the lines 434–438 is coupled to the keyboard buffer 74.

Also illustrated in FIG. 4c is a set-up circuit 450 for initiating the operation of the acquisition unit 10. The set-up circuit consists of a one-shot multivibrator 452 set by the output of an AND gate 454 coupled to a NAND gate 456. An output from the one-shot multivibrator 452 is coupled through an ID length state control 458 comprising switches 460 and 462.

Figure 4D:
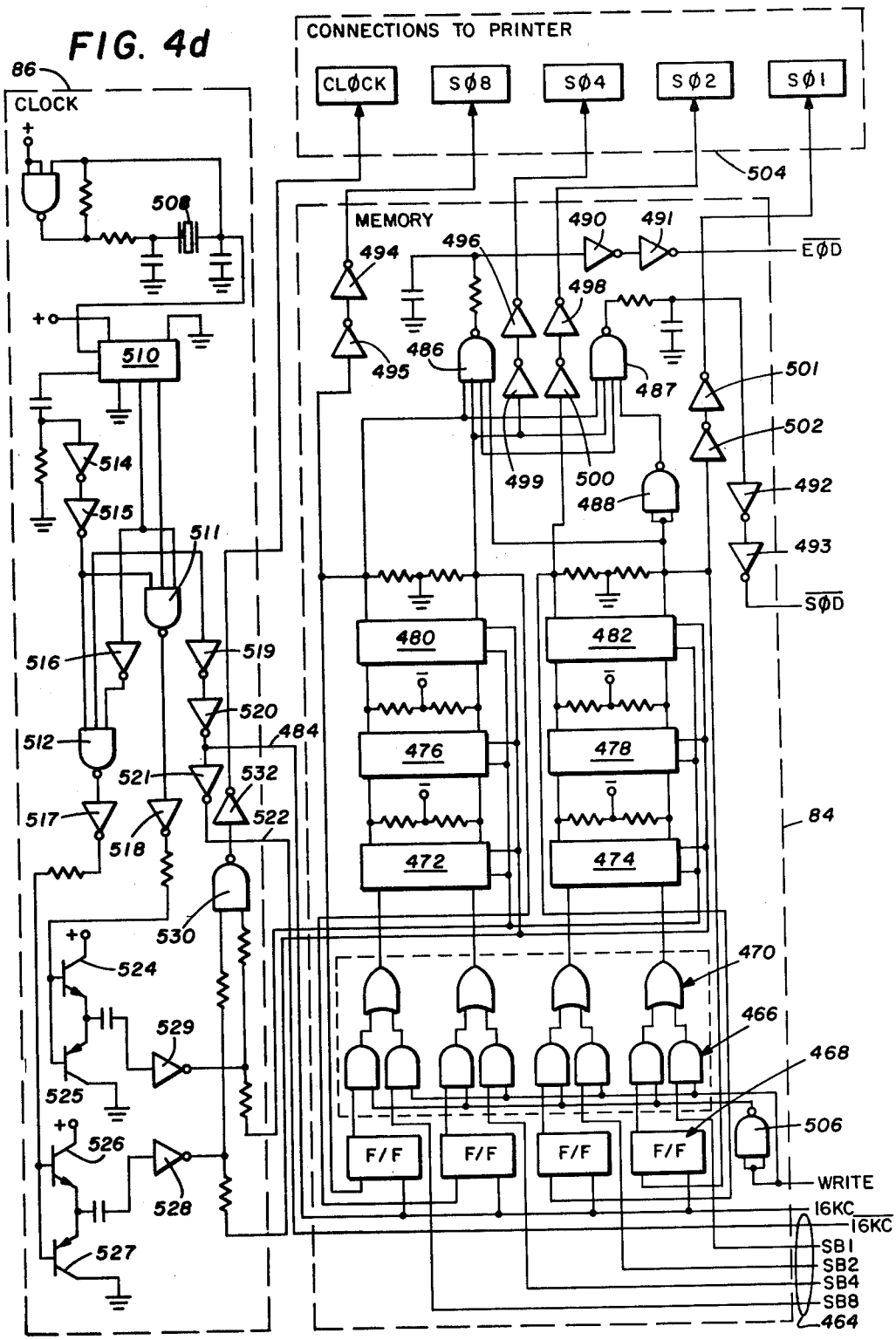

Referring to FIG. 4d, the memory 84 comprises an array of circulating registers responsive to clock pulses for continuously circulating data stored therein. Data to be stored in the memory 84 from the memory control 82 is transferred over data lines 464 otherwise identified as SB1, SB2, SB4 and SB8. These data lines individually connected to AND gates in an array 466 also including gates individually tied to the output of one of four flip-flops in an array 468. Pairs of AND gates in the array 466 are coupled to individual OR gates in an array 470 which in turn are connected in pairs to either dual shift register 472 or 474. The dual shift registers 472 and 474 are part of the main memory that also includes dual shift registers 476, 478, 480 and 482. Output lines from the dual shift registers 480 and 482 are coupled to logic for providing the EOD signal and SOD signal and also to logic for transferring the memory data to the system printer, as will be explained. In addition, the output lines of the dual shift registers 480 and 482 are coupled to the input of the flip-flops in the array 468 and it is this interconnection that produces recirculation of data through the memory. This recirculation is controlled at a clock rate generated on a line 484 as an output from the clock 86.

The logic for producing the EOD signal and SOD signal comprises NAND gates 486–488 and inverting amplifiers 490–493. Logic for coupling the output of the registers to the printer includes inverting amplifiers 494–496 and 498–502. The output data from the memory is coupled to the printer through terminal hardware 504.

Data is written into the memory 84 in response to a "write" signal generated as a result of actuating the RECORD switch 28 to generate a signal to a NAND gate 506. An output from the NAND gate 506, or the "write" signal from the memory control 82, is connected to one input of each of the AND gates in the array 466.

Clock signals for operating the entire acquisition unit 10 are generated by a clock 86 including a crystal 508. The crystal frequency steps a frequency divider 510 coupled to logic including NAND gates 511 and 512 along with inverting amplifiers 514–521. The output of the inverting amplifier 520 is the primary clock frequency for the system generated on the line 484, and the output of the inverting amplifier 521 is the logic inverse of the primary clock signal and is generated on a line 522.

Also forming part of the clock 86 are transistor switches 524–527 with the transistors 524 and 525 connected to inverting clock driver amplifier 529 and the transistors 526 and 527 connected to inverting clock driver amplifier 528. The outputs of the clock drivers 528–529 provide two phase non-overlapping clock signals to dual shift registers of the memory 84. The output of the clock drivers 528–529 are also coupled through a NAND gate 530 and an inverting amplifier 532 to the terminal hardware 504 for supplying a synchronizing clock to the printer.

Figure 4E:
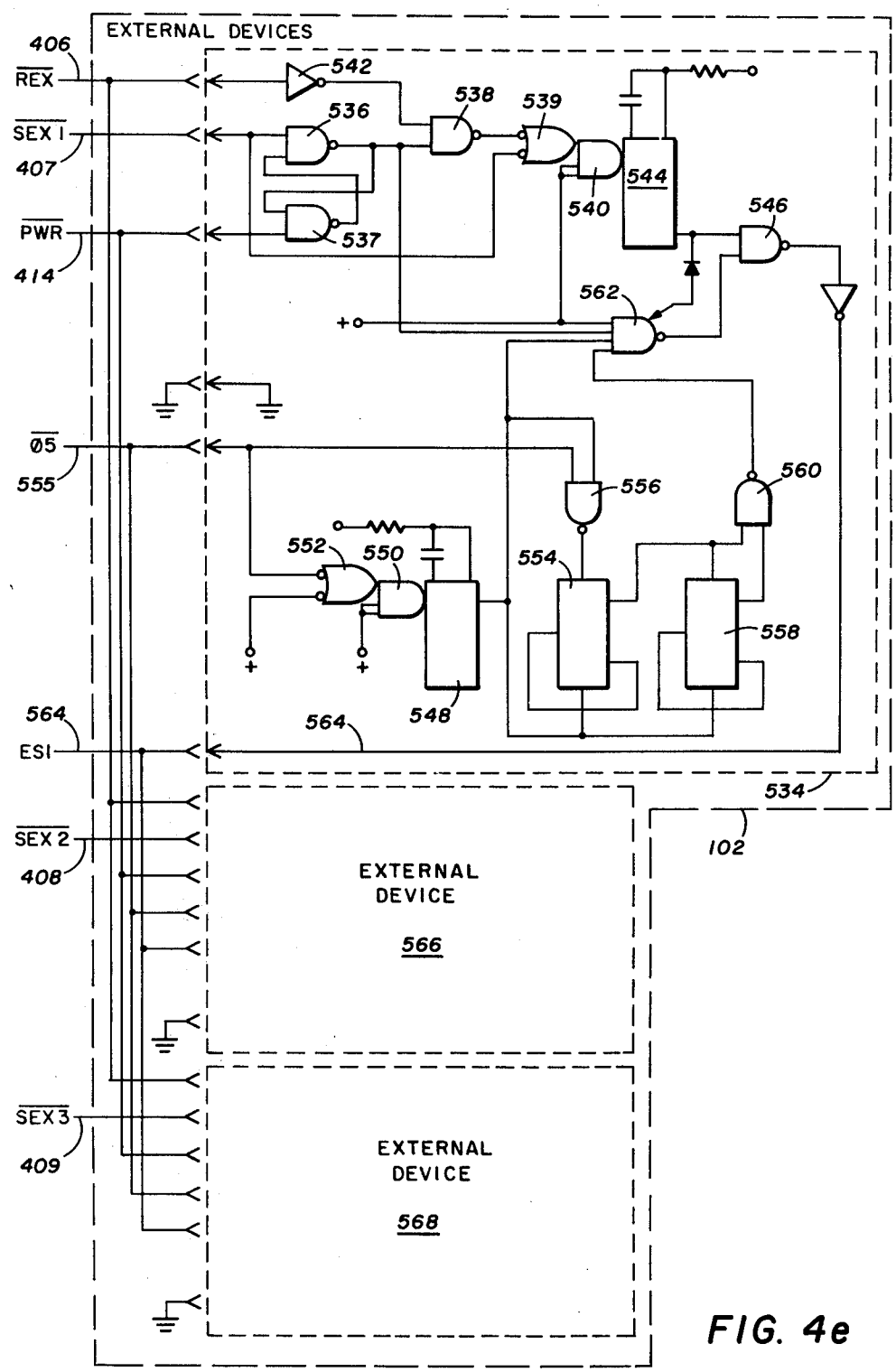

Referring to FIG. 4e, there is shown the external device block 102 with details of an illustrative external device 534. The external device 534 includes logic for responding to an inquiry from the state controller 6 and for producing the BCD data signals to the display register 78. Input signals $\overline{REX}$, $\overline{PWR}$, $\overline{\theta 5}$ are provided to the external device 534 if present and also to external devices 566 and 568 if present. Input signal $\overline{SEX1}$ is also provided to the external device 534 while external devices 566 and 568 receive input signals $\overline{SEX2}$ and $\overline{SEX3}$ respectively. All three external devices 534, 566 and 568 share a common output line ESI 564. In the idle state of the acquisition unit 10 the signal $\overline{PWR}$ is set to a logic level which causes all connected external devices to relinquish control of the common status and data line ESI 564. During its sequence of operation the state controller 66 generates control signals which are decoded by the decoder 398 and applied to the transistor 403 to generate a "select external device 1" ($\overline{SEX1}$) signal on the line 407. If external device 534 is connected to acquisition unit 10, it assumes control of the ESI line forcing it from a first logic level to a second logic level. This transition of the ESI line 564 from the first logic level to the second logic level is sensed by NAND gates 742 and 743 of the external input 104 as shown in FIG. 5l. Upon sensing the proper transition of the ESI line 564 the gates 742 and 743 generate an $\overline{EC}$ signal to the state controller 66 indicating that the first external device is connected. The external device maintains the ESI line 564 at the second logic level until it completes its measurement and is prepared to send its processed data to the acquisition unit. In the illustrative circuit this delay is simulated by the one-shot multivibrator 544. When the selected external device is ready to transmit its data it returns the ESI line 564 to the first logic level. When the state controller 66 advances its sequence to the point for accepting data from external devices and the selected external device has indicated that its measurement is complete, the NAND gate 747 of the external input 104 of FIG. 5l generates a logic signal ERDY to the serial data transfer control 94 of FIG. 5j. Upon receipt of the ERDY signal the data transfer controller generates a sequence of pulses $\overline{\theta 5}$ on the line 555 to the external device 102. The sequence of pulses on the $\overline{\theta 5}$ line are used as clock pulses by the external device to synchronize the transfer of its BCD data which it sends to the data acquisition device 10 on the ESI line 564. In addition to its collected data, the external device sends to the acquisition unit an identifying code for subsequent use by the printer 16 in properly identifying the origin of the data. The transmitted data is displayed in the display 22. At the operator's discretion the data measurement by the external device may be reinitiated by pressing the REPEAT switch 30 of the keyboard 24. This action causes a pulse on the $\overline{REX}$ line to the external devices and the external device which has been previously selected collects and transmits new data. Use of the RECORD switch 25 will transfer the data received from the external device to the memory 84. When the data from the first external device 534 is recorded a pulse generated on the $\overline{PWR}$ line will cause the first external device 534 to relinquish control of the ESI line.

In a similar manner additional external devices are interrogated and if attached will sequentially assume control of ESI line 564 indicating their presence. Up to three external devices may be attached to the acquisition unit 10.

The structure of an illustrative external device is shown as block 534 of FIG. 4e. Logic including NAND gates 536–539, and AND gate 540 and an inverting amplifier 542 receives the commands from the state controller 66 to set a one-shot multivibrator 544. A ready signal is generated at the output of the one-shot multivibrator 544 through a NAND gate 546 and a count enable signal is generated at the output of one-shot multivibrator 548 having an input interconnected to an AND gate 550 and a NAND gate 552, the latter receiving through line 555 a clock from the divider and serial data transfer controller 94. Also receiving a clock is a flip-flop 554 through a NAND gate 556. The flip-flops 554 and 558 constitute a binary counter having outputs coupled through a NAND gate 560 to a NAND gate 562 in turn tied to the NAND gate 546 to generate an external signal input to the input logic 104 on a line 564. This signal is initiated by the control signals on lines 406, 407 and 414 and is synchronized with the clock signal on line 555. External devices 566 and 568, shown only in block form, may be similar to the external device 534.

Temperature, respiration rate and pulse rate data along with information generated by external devices are processed through the acquisition unit 10 to the display 22 and subsequently stored in the memory 84.

The entire sequence of operation of the acquisition unit 10 is under the control of the state controller 66 and various logic networks interconnected thereto. The state controller essentially controls everything in the acquisition unit through the various modes including the identification mode, pulse rate acquisition mode, respiration rate acquisition mode, the temperature acquisition mode and a mode for receiving information from external devices.

Referring to FIGS. 5a–k, there is shown logic circuitry for the state controller 66 and interconnected logic networks within the dotted outline 560 of FIG. 3. Although a logic element by element description of FIG. 5 will not be given herein, a basic discussion of the diagram will be presented to enable a better understanding of the acquisition unit 10. Standard logic symbols and interconnecting line format are utilized in the logic circuitry of FIG. 5.

Figure 5A:
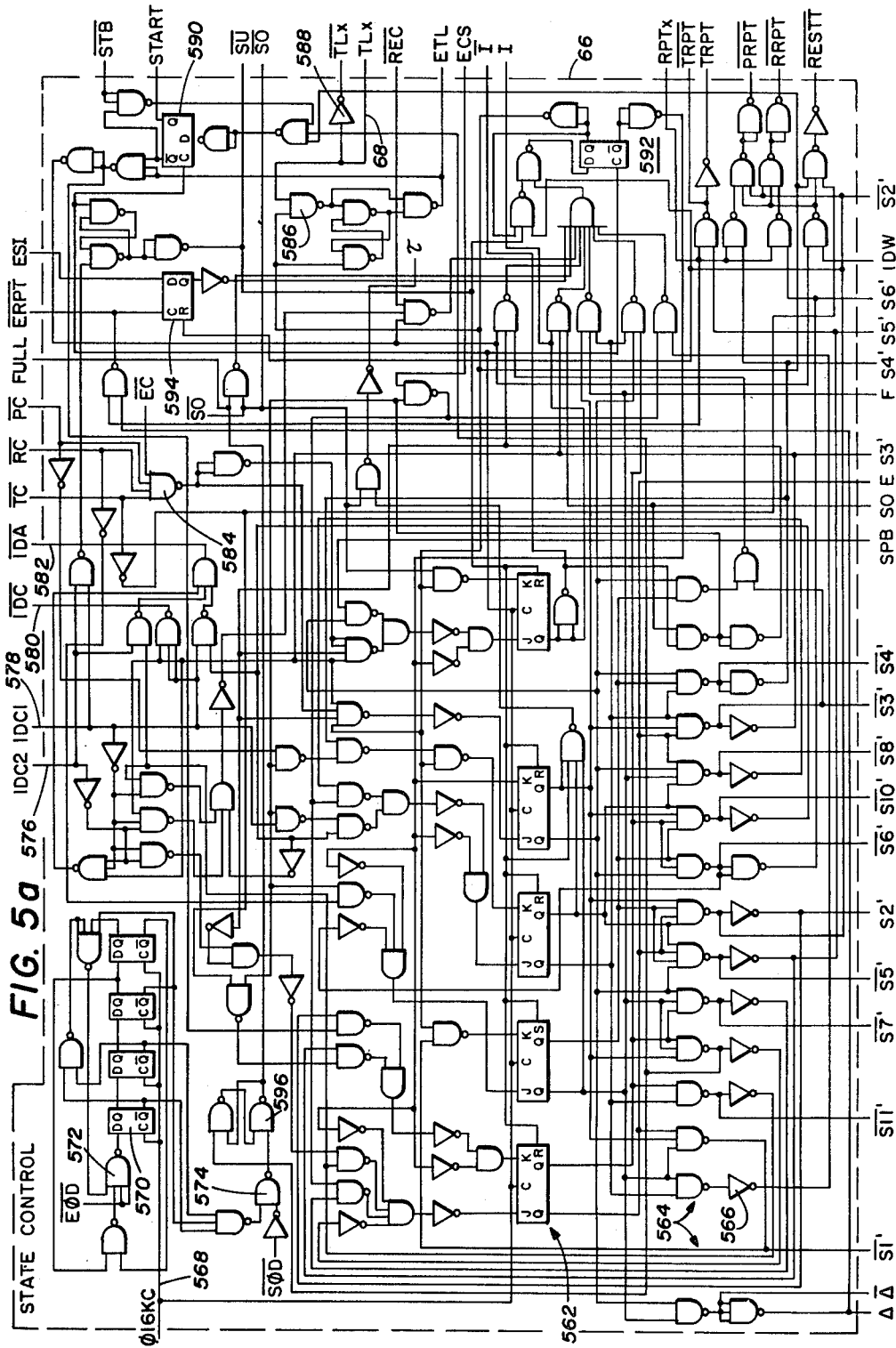

Referring to FIG. 5a, there is shown a logic diagram for the state controller 66 wherein the five flip-flops 562 generate the control bits for sequentially operating the acquisition unit 10 through the various modes. These control bits are decoded in NAND gate logic 564 interconnected to inverted amplifiers 566 to generate all the mode control signals for the acquisition unit. Primary clock pulses for the state controller are applied thereto over a line 568.

An end-of-data signal from the memory 84 is applied to NAND gate 572 and a start-of-data signal is applied to a NAND gate 574 as part of the NAND logic associated with the flip-flops 570 and NAND gates 596 for detecting the full memory condition.

A feature of the acquisition unit 10 is that it will accept varying length identification codes from a four digit code up to a 12 digit code. Control signals on the lines 576 and 578 are generated to the state controller 66 to identify the length of the ID code. When a four digit ID code is utilized, signals on both the lines 576 and 578 are at a logic level to set the flip-flops 562 for a shortened ID mode operation. For the eight digit ID code, a logic signal is generated on the line 576 as a control bit to the flip-flops 562. For a twelve digit ID code, a signal is generated on the line 578 to set the flip-flops 562 to enable a longer time in the ID mode. The logic signals on lines 576 and 578 are programmed by setting ID length state switches 460 and 462 of FIG. 4c. The state controller 66 in turn generates control bits on lines 580 and 582 to the memory control 82 to set the logic of the memory control to record the proper ID code length identifiers in the memory 84.

Also establishing control of the flip-flop 562 is the output of a NAND gate 584 receiving the $\overline{TC}$, $\overline{RC}$ and $\overline{PC}$ probe connection indications from the temperature probe, respiration rate probe and pulse rate probe, respectively, and the $\overline{EC}$ external device connection indication from the external input circuit 104. It is the NAND gate 584 and additional logic connected to the $\overline{TC}$, $\overline{RC}$, $\overline{PC}$ and $\overline{EC}$ signals that determines whether the acquisition unit will proceed in the temperature, respiration rate, pulse rate, or external modes. The $\overline{TC}$ signal, $\overline{RC}$ signal and $\overline{PC}$ signal are received directly from the temperature circuit 60, the respiration rate circuit 62 or the pulse rate circuit 64, respectively. The $\overline{EC}$ signal is extracted from the external device signal line 564 by the external input circuit 104.

As discussed previously, the acquisition unit becomes operational when the temperature sensor passes a predetermined temperature level. The state controller 66 receives the temperature actuating signal at a NAND gate 586 and inverts this signal through an inverting amplifier 588 for connection to the temperature counter 98 of FIG. 5k. A start signal is also applied to the temperature counter 98 from a flip-flop 590 as part of logic circuitry including NAND gate 726 coupled to receive control pulses from the state controller 66.

Figure 5C:
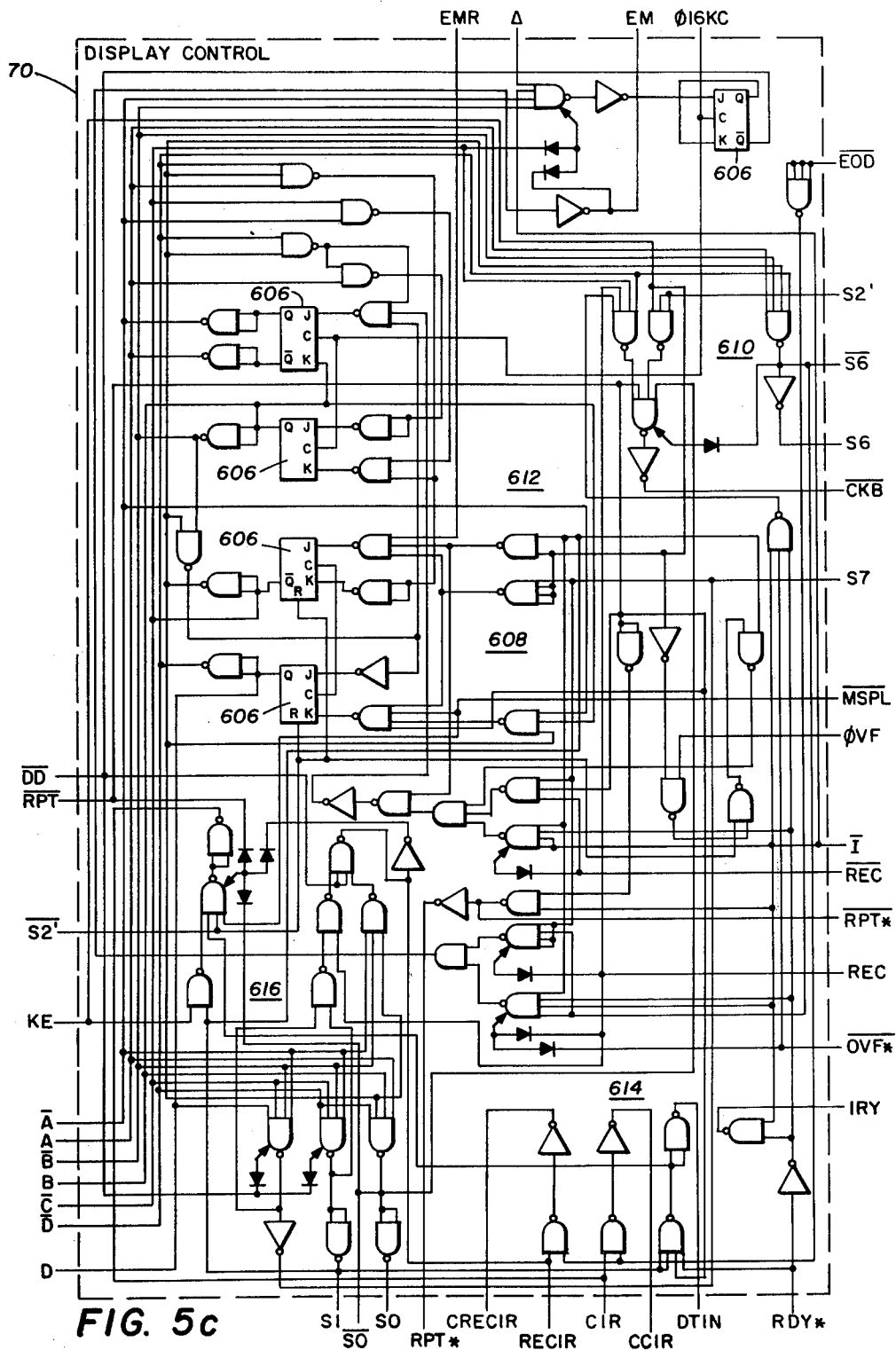
Figure 5D:
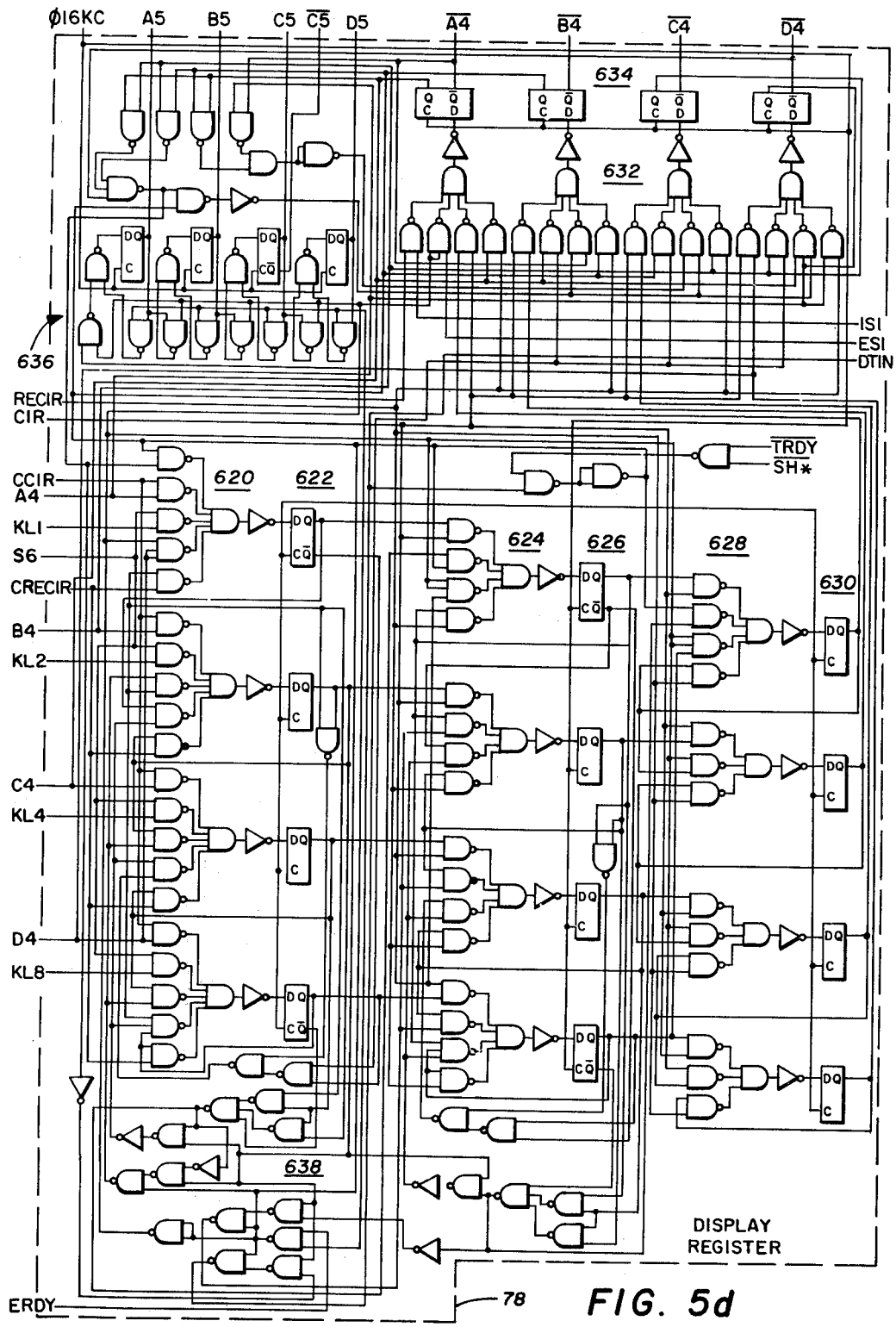
Figure 5E:
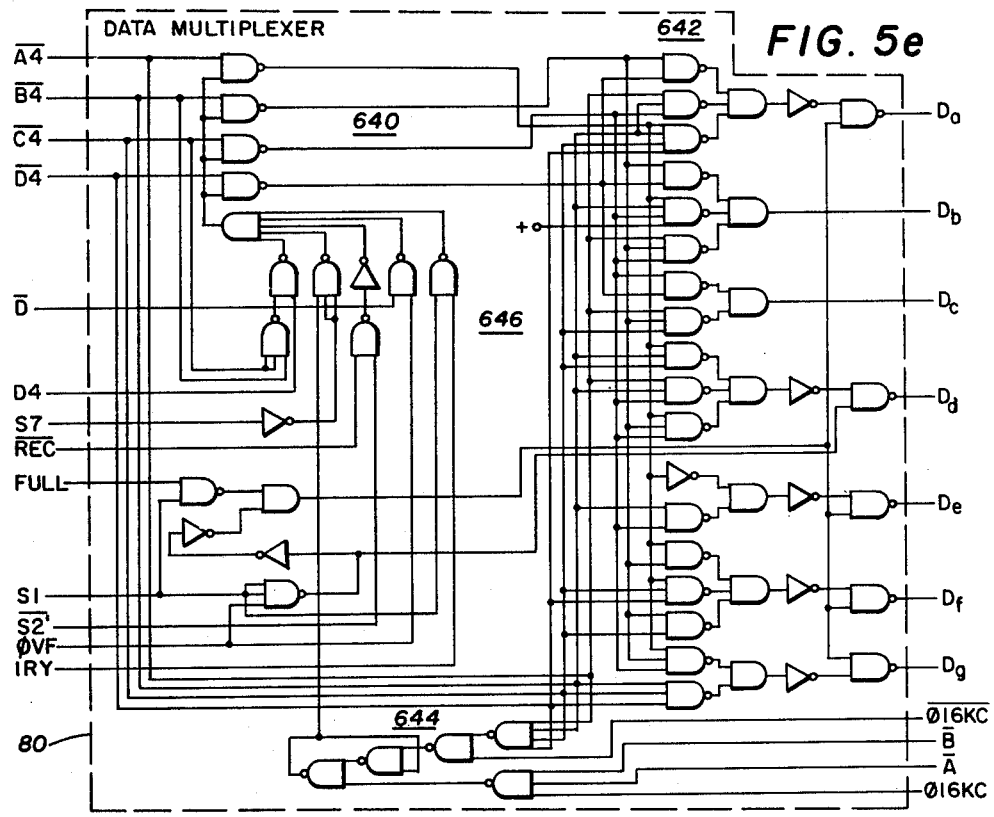
Figure 5F:
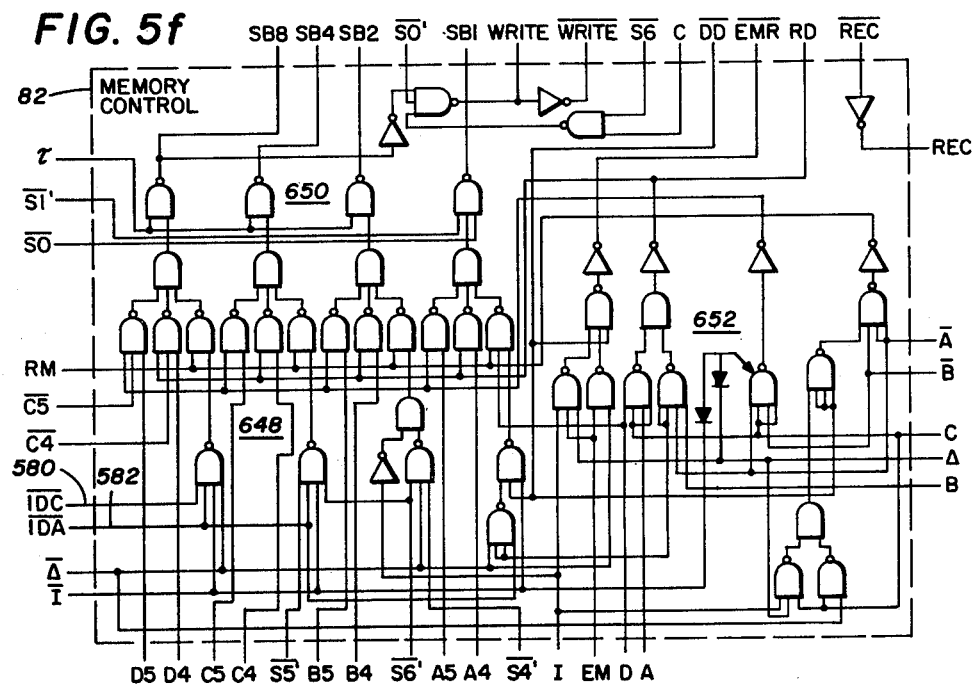
Figure 5G:
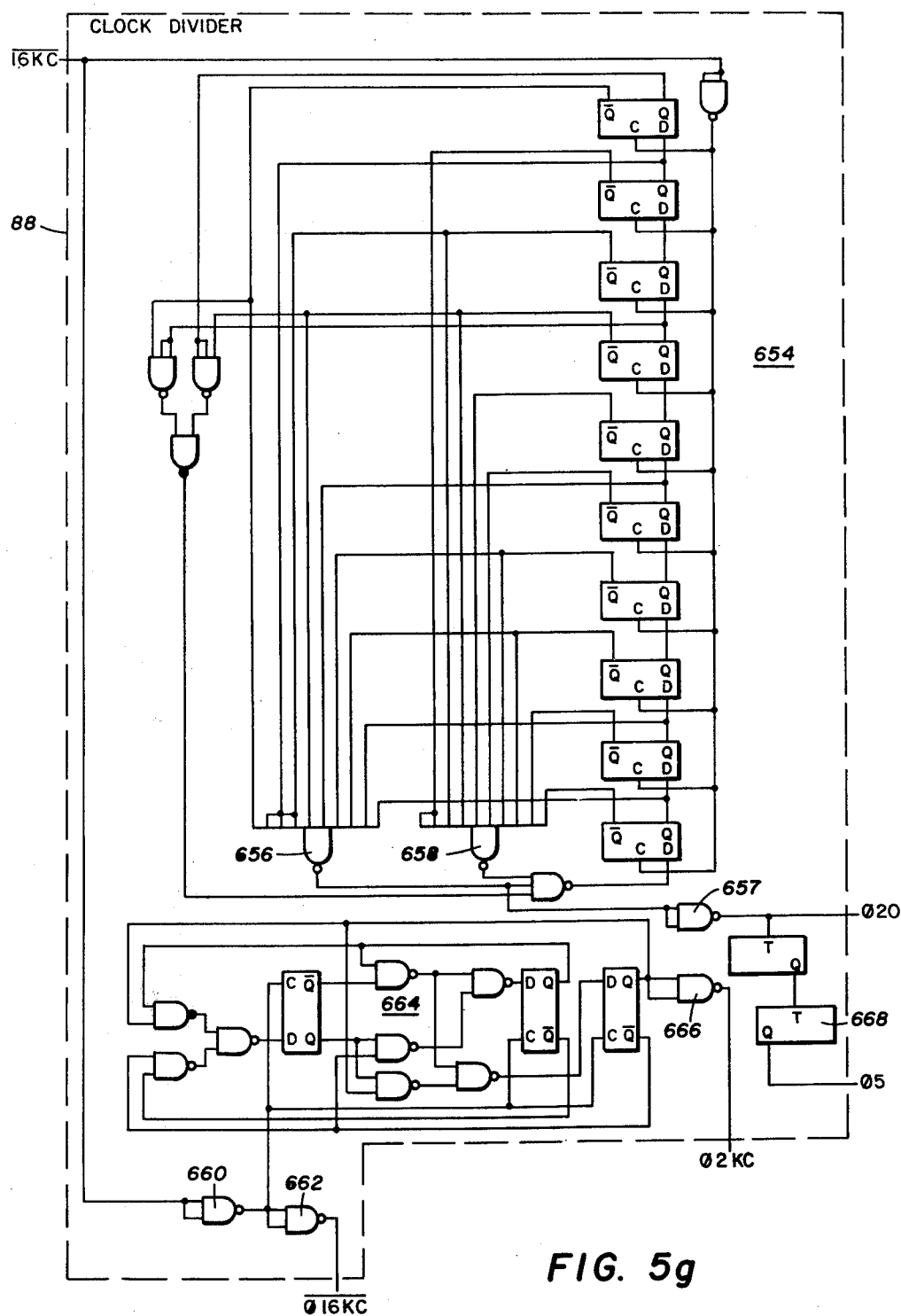
Figure 5H:
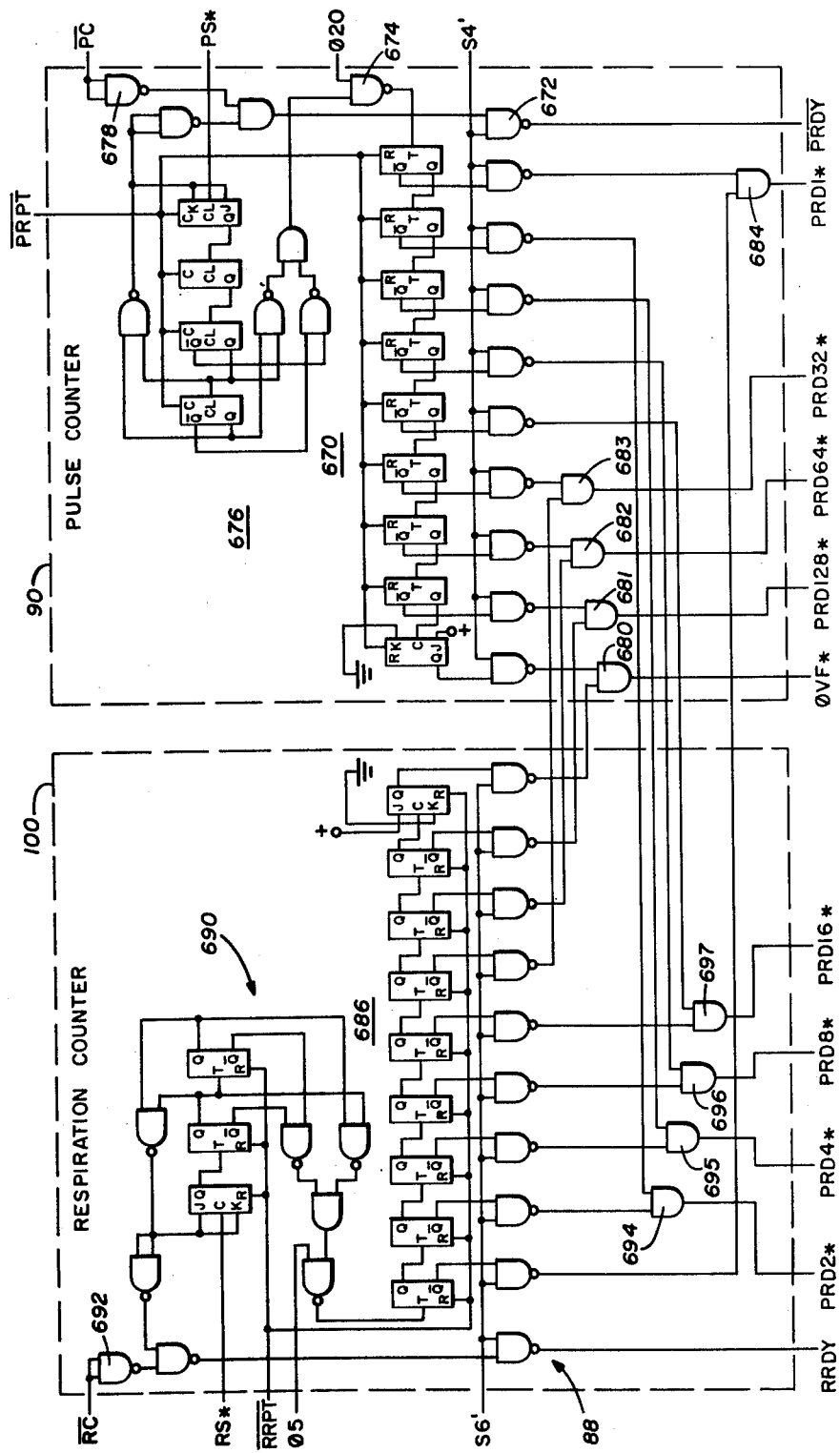

NAND gate logic 592, as part of the state controller, provides various control signals to the pulse counter 90 and the respiration rate counter 100, both illustrated in FIG. 5h, and the temperature counter 98 to reset all the counters between patients and to reset the appropriate one when the REPEAT switch 30 is actuated. When operating in the external mode, a flip-flop 594 receives an ESI signal from the external device. The flip-flop 594 causes the state controller 66 to return to its idle state if the operator attempts to repeat a data measurement from an external device which has been disconnected from the acquisition unit 10. Also generated by the state controller 66 is a memory full signal at a NAND gate 596 coupled to the data multiplexer 80 of FIG. 5e for generating an indication in display 22 when memory 84 is filled to capacity.

Referring to FIG. 5b, there is shown internal logic for the keyboard buffer 74 receiving encoded data signals $\overline{K8}$, $\overline{K4}$, $\overline{K2}$, $\overline{K1}$ and PK16 from the keyboard encoder 72. Included in the logic for the keyboard buffer are NAND gates 598 for providing binary encoded data on lines KL1, KL2, KL4 and KL8 to the display register 78 of FIG. 5d through the gate 76. Also included within the keyboard buffer 74 for internal sequencing control are flip-flops 600 and 602 and associated NAND gate logic. Various control signals are transferred between the keyboard buffer 74 and the state controller 66. These include a SPB signal, an $\overline{REC}$ signal, an I signal and an $\overline{SU}$ signal coupled to the flip-flops 600 and 602. Control signals generated by the keyboard buffer 74 are provided at the outputs of NAND gates 604.

Another control section of the logic of FIG. 5 is the display control 70 wherein signals $\overline{S2'}$, SO, RPT*, $\overline{REC}$, I, S2' and Δ are transferred between the state controller and the display control.

Referring to FIG. 5c, there is shown logic circuitry for the display control 70 including four flip-flops 606 and associated NAND gate logic for generating the A, $\overline{A}$, B, $\overline{B}$, C, D, $\overline{D}$ and $\overline{DD}$ signals coupled to the data multiplexer 80 of FIG. 5e and the memory control 82 of FIG. 5f. Logic circuitry for driving the flip-flops 606 includes NAND gates 608 responsive to the REC signal and the $\overline{REC}$ signal from the keyboard buffer 74. These are the record signals for transferring data in the display register 78 through the memory control 82 to the memory 84. Timing signals to the display logic are applied thereto through NAND gate arrays 610 and 612. Also included as part of the display control 70 is logic 614 coupled to the display register 78 of FIG. 5d. NAND gate logic 616 is coupled to the flip-flops 606 and provides the S1, SO and $\overline{SO}$ signals with the S1 signal coupled to the data multiplexer 80 and the memory control 82, the SO signal connected to the memory control 82 and the data transfer controller 94 of FIG. 5j and the state controller 66, and the $\overline{SO}$ signal to the state controller 66. Also generated by the display control 70 is an EM signal to the memory control 82.

Referring to FIG. 5d, there is shown logic circuitry for the display register 78 controlled by signals generated at the logic 614 of FIG. 5c. The display register 78 includes NAND gate logic 620 coupled to the keyboard buffer 74 of FIG. 5b, and in particular to the NAND gates 598. Connected to the outputs of the NAND gates 620 is an array of flip-flops 622 interconnected to NAND gate logic 624. The outputs of the NAND gates 624 are coupled through four flip-flops 626 to NAND gate logic 628. In turn, the outputs of the NAND gate logic 628 are coupled through four flip-flops 630 to NAND gate logic 632. From the NAND gate logic 632, the signals are applied to four flip-flops 634 having outputs $\overline{A4}$, $\overline{B4}$, $\overline{C4}$ and $\overline{D4}$ connected to the data multiplexer 80 of FIG. 5e.

Also included as part of the display register 78 is NAND gate logic 636 coupled to the memory control 82. As connected, the display register 78 comprises a recirculating register and includes NAND gate logic 638 for controlling the binary to BCD conversion process. Also applied to the display register 78 at the NAND gate logic 632 are signals ISI, ESI and DTIN.

Referring to FIG. 5e, data signals generated by the display register 78 are coupled to the data multiplexer 80 at NAND gate logic 640 having outputs coupled to decoding logic 642. The decoding logic converts the output of the display register 78 into a signal format for driving the display 22. Also forming part of the data multiplexer 80 is NAND gate logic 646 responsive to control signals for generating the various indicator messages at the display 22, as explained previously. NAND gate logic 644 is responsive to the system clock pulses, the displayed data, and display control 70 to prevent the display of nonsignificant leading zeros in the display register 78.

Referring to FIG. 5f, there is shown logic circuitry for processing data from the display register 78 for transfer to the memory 84. Input data to the memory control 82 is coupled to NAND gate logic 648 that in turn drives a NAND gate array 650 generating SB1, SB2, SB4 SB8 and WRITE signals to the memory 84. In addition to receiving data from the display register 78, the memory control 82 connects to the state controller 66 and the display control 70. Thus, the memory control 82 provides control logic for addressing the memory 84. Forming part of the logic for the memory control 82 is a NAND gate array 652 responsive to signals from the display control 70.

The entire acquisition unit 10 is sequenced in accordance with clock pulses generated at the clock 86 and divided by the clock divider 88. Referring to FIG. 5g, there is shown logic circuitry for the clock divider 88 including a flip-flop array 654 each having outputs selectively coupled to a NAND gate 656 or a NAND gate 568. NAND gate 657 provides a 20 Hz clock signal for system timing requirements.

Also forming part of the clock divider is a NAND gate 660 generating the primary clock frequency of 16 kilocycles for the acquisition unit and at the output of a NAND gate 662 there is generated a 16 kilocycle clock 180 electrical degrees displaced from the output of the gate 660. The output from the NAND gate 660 is coupled to flip-flops and NAND gate logic 664 to generate a 2 kilocycle clock at the output of a NAND gate 666. Also provided by the clock divider 88 is a 5 Hz timing signal at the output of a flip-flop 668. The primary 16 KHz clock is coupled to the logic circuitry of FIGS. 5b, c, d, e, j and k and the 5Hz timing signal from the flip-flop 668 is applied to the logic of FIGS. 5h and 5m. The 20Hz timing signal from NAND gate 657 is coupled to the logic of FIG. 5h. The 2KHz clock signal is coupled to the temperature counter of FIG. 5k and the $\overline{16KC}$ signal is applied to the data multiplexer 80 of FIG. 5e.

After completion of the ID mode, the acquisition unit advances to the pulse mode wherein pulses generated at the output of the pulse circuit 64 are applied to the pulse counter 90. Referring to FIG. 5h, there is shown a logic diagram of the pulse counter 90 including a register composed of nine flip-flops 670 each having an individual output tied to one input of a NAND gate in an array 672. The flip-flops 670 are stepped by the output of a NAND gate 674 as part of logic including four flip-flops 676 and associated NAND gates.

Pulse signals generated by the analog circuit 64 are coupled to the first flip-flop of the array 676 to advance the counter in accordance with a patient's pulse rate. Operation of the counter is controlled by a $\overline{PC}$ signal applied to NAND gate 678 and a $\overline{PRPT}$ signal connected to flip-flop arrays 670 and 676. In the pulse rate mode, the signal S4' is applied to the NAND gate 672 to transfer the total count to the pulse and respiration rate divider 92 of FIG. 5i. The pulse rate data is generated by the counter 90 at the output of the NAND gates 680–684 and 694–697.

Following the pulse mode, the acquisition unit advances to the temperature mode and then to the respiration rate mode and a logic diagram of the respiration rate counter 100 is also detailed in FIG. 5h. Both the counters 90 and 100 are similar with the respiration rate counter including an array of flip-flops 686 having individual outputs connected to one input of a NAND gate in an array 688. The respiration rate pulses from the analog circuit 62 are applied to the first flip-flop in an array 690 having associated NAND gate logic including a NAND gate 692 responsive to the probe connection signal from the circuit 62.

In the respiration rate mode a S6' signal is applied to the NAND gates 688 to transfer the count in the flip-flops 686 to the divider 92. The total count from the counter 100 is generated at the output of NAND gates 694–697 and 680–684.

Figure 5I:
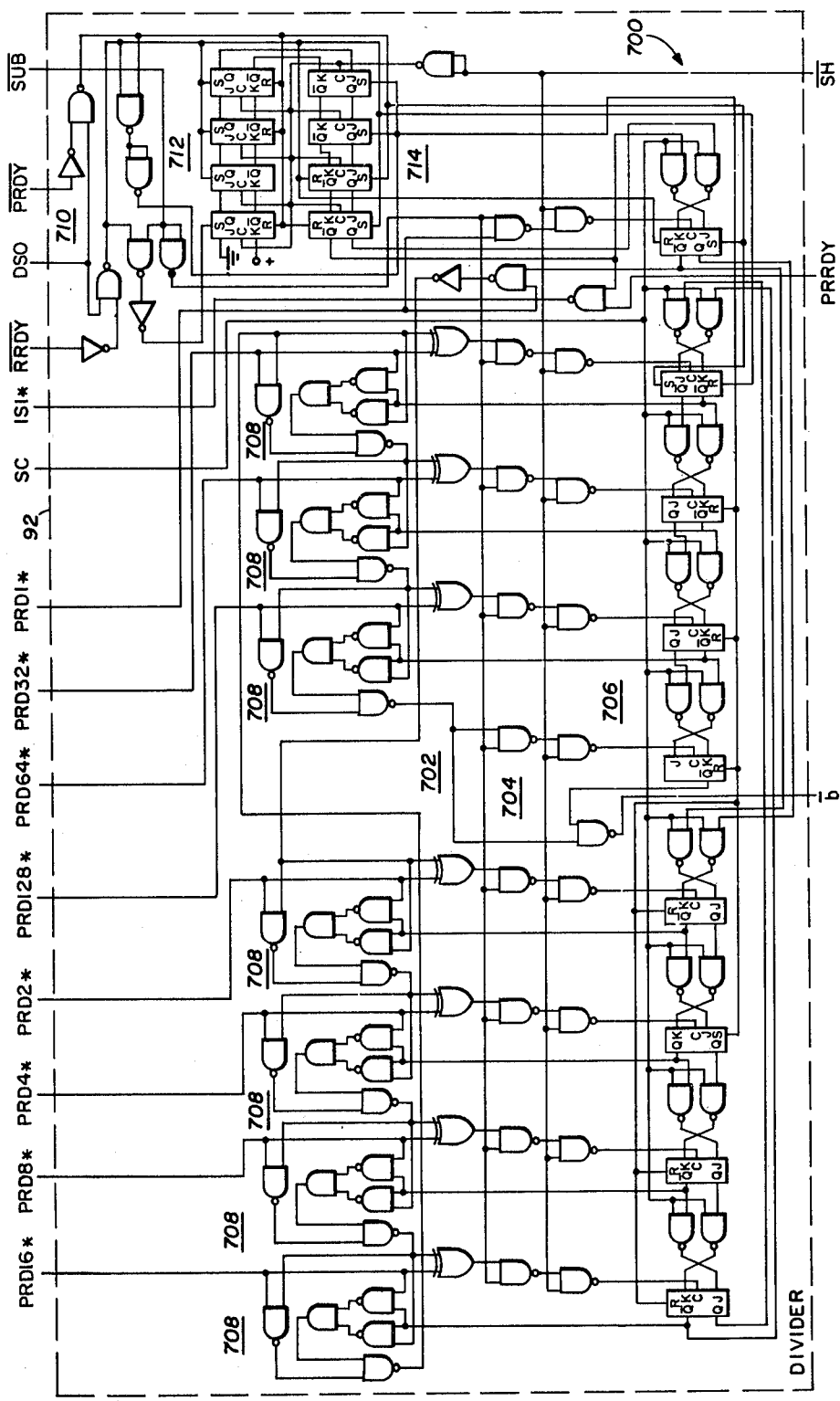

At the end of the time interval during both the pulse rate mode and the respiration rate mode, the total count from the counter 90 or the counter 100 is transferred to the pulse rate and respiration rate divider 92 as shown in FIG. 5i. FIG. 5i is a logic diagram of the divider 92 and includes a register of flip-flops and interconnected NAND gates in an array 700. The total count data from either the counter 90 or 100 is applied to the array 700 through an EXCLUSIVE OR gate array 702, NAND gate logic 704 and NAND gate logic 706. Also coupled to the output lines of the counters 90 and 100 and the EXCLUSIVE OR gate array 702 is NAND gate logic in seven arrays 708.

Operationally, the NAND gate arrays 708 and the EXCLUSIVE OR gate arrays 702 along with the NAND gate logic 704 and 706 combine with the array 700 to complete the division function as described earlier to provide binary data to the display register 78 for a visual presentation in the display 22. This transfer of data is controlled by the data transfer controller 94 by signals coupled to logic including NAND gates 710 and flip-flops 712 and 714.

Figure 5J:
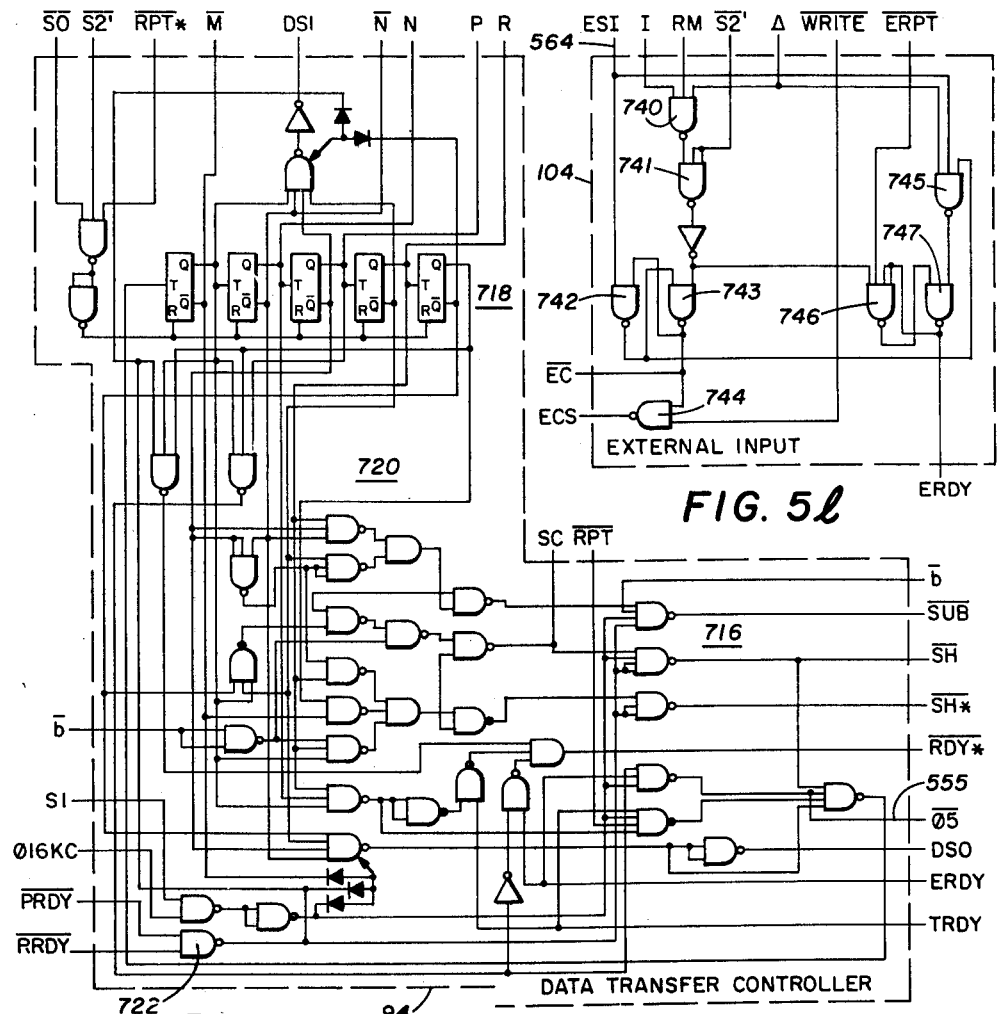

Primarily, the divider 92 is sequenced by the controller 94 in the various modes as established by the state controller 66. Referring to FIG. 5j, there is shown a logic diagram for the data transfer controller 94 generating control signals at the output of NAND gates in an array 716. The NAND gates in the array 716 have inputs coupled to terminals of an array of five flip-flops 718 and NAND gate logic 720.

Figure 5M:
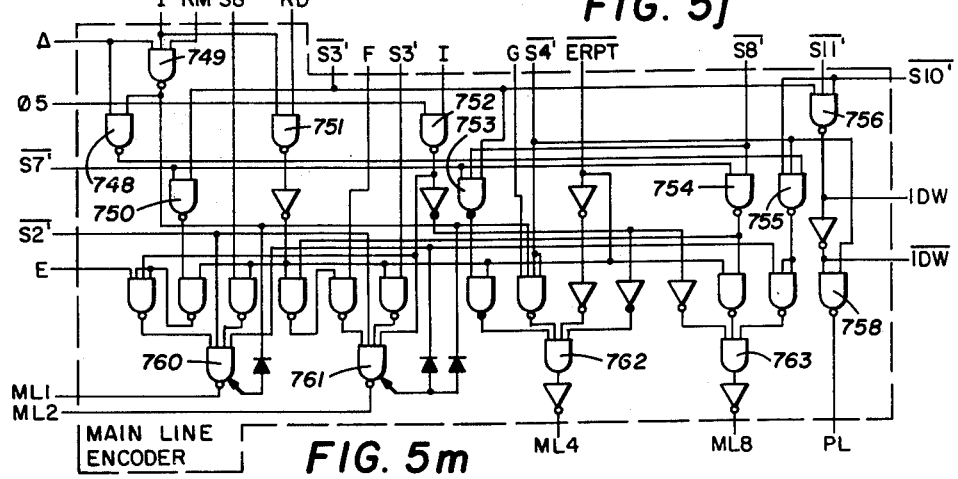
Figure 5K:
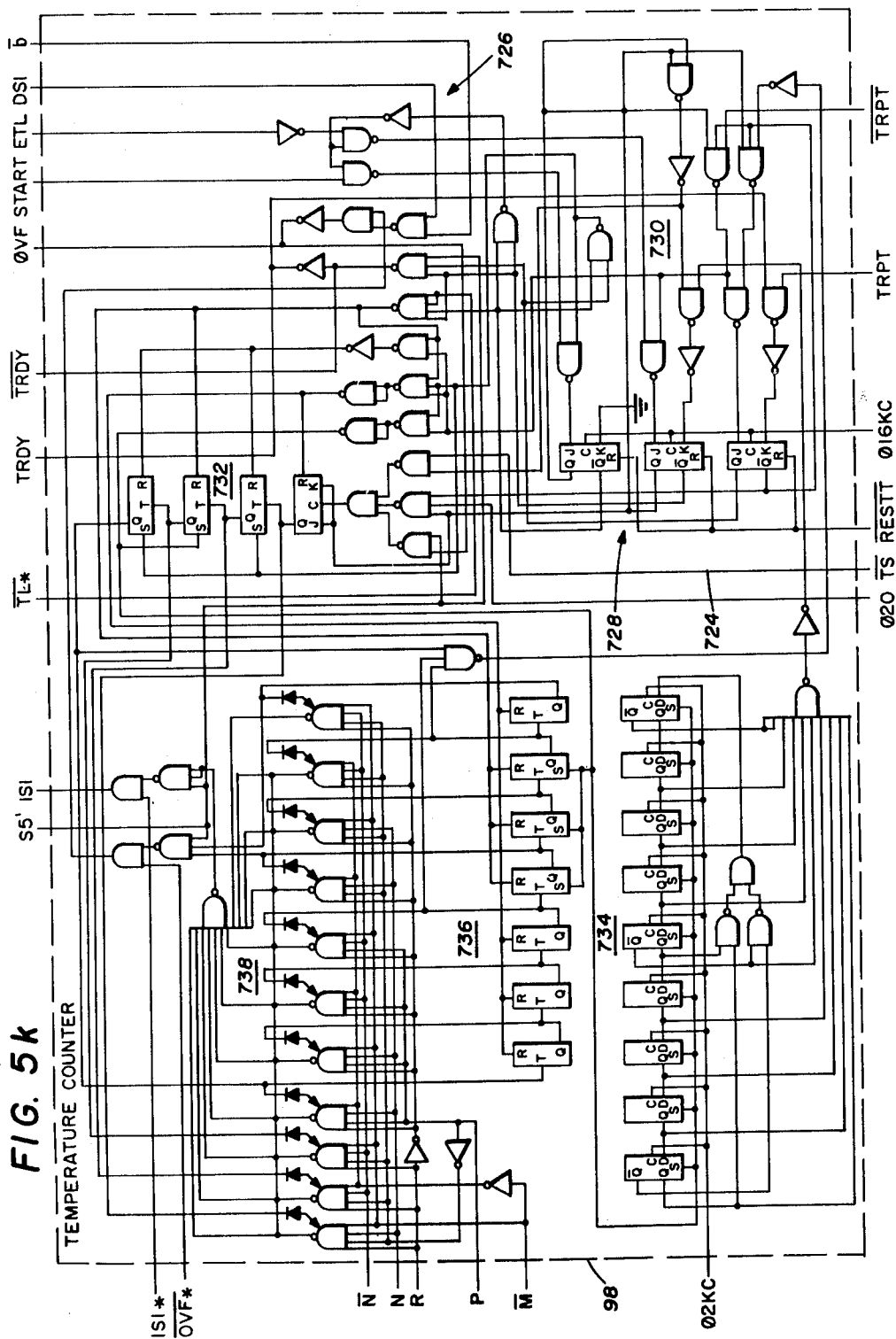

Input control signals from the state controller 66 are received at the flip-flop array 718 which also generates N, $\overline{N}$, $\overline{M}$, P, R, $\overline{b}$, and $\overline{DS1}$ signals to the temperature counter 98 of FIG. 5k. The flip-flop array 718 is also coupled to the NAND gate logic 720 which receives the primary clock signal and a pulse rate and respiration rate ready input at a NAND gate 722.

In the normal sequence of operation of the acquisition unit 10, the unit enters the temperature mode following the pulse mode. Frequency signals produced by the temperature circuit 60 are applied to the temperature counter 98 that is actuated for a predetermined time interval. This time interval is generated by flip-flop array 734.

Referring to FIG. 5k, there is shown a logic diagram of the temperature counter 98 receiving temperature related frequency signals on a line 724 coupled to selected NAND gates in an array 726. Also coupled to the NAND gates of the array 726 are control signals from three flip-flops 728 having inputs connected to a NAND gate array 730. Connected to the NAND gate array 730 is the TRPT signal and the $\overline{TRPT}$ signal from the state controller 66. These signals as applied to the flip-flops 728 are coupled to the NAND gate array 726 for stepping a counting register comprising flip-flop arrays 732, 734 and 736. A totalized count as generated in the flip-flop arrays 732 and 736 is applied to a NAND gate array 738 that receives control signals from the data transfer controller 94.

Also applied to the temperature counter 98 is the temperature activating signal (TL*) applied to selected gates of the array 726. This array of NAND gates 726 also receives a START signal and generates a temperature ready TRDY signal and a $\overline{TRDY}$ signal to the controller 94 and the display register 78, respectively. Both the 16 kilocycle clock and the 2 kilocycle clock are coupled to the temperature counter 98 for sequencing thereof.

During the external mode operation of the acquisition unit 10, externally generated data from devices 102 are transferred through the external input 104 to the gate 96. Referring to FIG. 5l, there is shown logic for the external input circuit 104 including NAND gates 740–747. The NAND gates 740, 744, 745 and 746 are coupled to the input control signals and the NAND gates 743, 744 and 747 generate output signals to other sections of the logic of FIG. 5. Basically, the external input circuit 104 is logic for determining the status of the external device 102.

Although not specifically shown in FIG. 3, the line encoder of FIG. 5m is associated with the data multiplexer 80 for converting the timing and control signals from the state controller 66 into control signals to the display 22 and to the external devices 102 and to the switched power supply 108. Input signals are connected to the line encoder at NAND gates 748–756 and these gates in turn are coupled to inputs of a NAND gate array 758 for decoding into ML1, ML2, ML4 and ML8 signals to the display 22 and external devices 102 as shown in FIG. 4b and PL to the switched power supply 108 of FIg. 4a. The output signals from the line encoder are generated at the terminals of NAND gates 760–763 and 758.

Referring to FIG. 6, after an attendant has made a round and stored in the memory 84 the pulse rate, temperature and respiration rate of patients under his control, or after the memory 84 is completely loaded, the acquisition unit is placed in one of the two chutes 40 or 42 of the printer 16 illustrated by a block diagram wherein the print buttons 44 and 46 are part of block 101 connected to random logic 103.

Basically, the printer 16 is a computer controlled sequential comparison system wherein the computer program is hard wired logic including a master read-only-memory (ROM) 105 and a subroutine read-only-memory 107. The read-only-memories 105 and 107 store the program for sequentially operating a comparison network to generate control signals to a character printer such as the Suwa Seiko Model EP101-S. Summarily, the read-only-memories 105 and 107 operate as follows: the read-only-memory 105 contains the main working program which includes instructions for addressing the read-only memory 107 to select a subroutine stored therein. Addressing the read-only-memory 105 is accomplished in one of three ways: (1) by data stored in the memory itself, (2) by selecting an address stored in a jump table located at the last fourteen words of the memory 105, or (3) by incrementing the address register of the read-only-memory 105. The read-only-memory 107 contains the subroutines called for by the memory 105 and when so specified by a particular subroutine, the output of the memory 105 is applied to the data bus through the ROM 1 output buffer 151. The subroutines of the read-only-memory 107 direct the functions of the printer such as performing all data transfers into the printer. Such transfers include reading data from the acquisition unit 10 or the lever switches 135 including the date switch 52 and the time switch 54. In addition, the subroutines of the read-only-memory 107 provide instructions for storing data in a random access memory 109, reading data from the random access memory and other functions to complete the printing of hard copy patient labels 18. Subroutines of the read-only-memory 107 are utilized through the use of decoders 111, 113 and 115 which control data lines 117 and 119 to the random logic 103.

Inserting an acquisition unit 10 into either the chute 40 or 42 of the printer 16 interconnects the memory 84 to interface circuitry 121 including an input buffer 123 and control lines 125 and 127. The input buffer 123 interconnects an acquisition unit to data selector logic 129 having an output line coupled to a bus tie-in 131. Also connected to the bus tie-in is a data buffer 133, the lever switches 135, and decoding logic 137, the latter also connected to the random logic 103. Data transferred through the bus tie-in 131 is transferred over a line 139 connected to comparator logic 141, a random access memory (RAM), address register 145, a RAM input register 143 and a read-only-memory address register 147.

Various sequencing operations of the printer are controlled by instructions from the random logic 103 as generated on a line 149 having interconnections to the register 145, the data selector 129, and the RAM input register 143 in addition to terminations at the lines 125 and 127.

As mentioned, sequencing of the operation of the printer is primarily under the control of the read-only-memory 105 and secondarily under the control of the read-only-memory 107. Enabling instructions to the memory 105 are received through the register 147 and control instructions from the memory are coupled through a buffer 151 to a word detector 153 and data select logic 155. Also coupled to the output buffer 151 is the address register 147 for addressing the memory 105 by data stored therein. Instructions from the read-only-memory 105 for the read-only-memory 107 are coupled through the data select logic 155 to a read-only-memory address register 157. Selected subroutines in the memory 107 provide instructions to the decoders 111, 113 and 115 through an output register 159.

Control signals to the character printer (not shown) and timing signals for operation of the printer are connected to the random logic 103 through printer interface logic 163. The logic 163 includes a trigger magnet controller 161 generating energizing signals to individual print hammer solenoids for producing a printing action on the labels 18. The number of trigger magnet controllers 161 depends on the number of columns possible to be printed by the character printer. In addition, the random logic 103 provides a control signal to paper feed logic 167 providing a voltage for controlling the movement of the labels 18 past the character printer. Timing signals generated by the character printer are applied to shaping circuits 169 to provide clock signals to the random logic 103 to synchronize the operation of the comparison system with the actual printing operation.

A clock 171 provides a primary clock for the printer through the random logic 103. Since the printer 16 is synchronized with the operation of the acquisition unit 10, the random logic 103 provides control signals to the clock 171.

Referring to FIG. 7, the printer 16 remains in an idle mode until an acquisition unit is inserted into either chute 40 or 42 thereby completing a connection between the acquisition unit 10 and the interface 121. Initially, the printer, through instructions from the memory 105, sequences to step 173 to check the condition of a status register located in decoding logic 137 to determine if the acquisition unit 10 is inserted into either chute 40 or 42 and the associated PRINT button has been pressed. If inquiry 173 produces a positive response, the printer advances to step 183 where system registers are initialized and the contents of the status register of random logic 103 modified so that subsequent inquiry 175 also results in a positive response. To test the condition of the status register, ROM 105 addresses ROM 107 to cause a comparison of a code in the register 143 with the code stored in the status register. This is completed by a subroutine of ROM 107 transferring a code from ROM 105 to the register 143 which is then compared in a comparator 141 with the code from the status register of random logic 103.

After the PRINT button has been actuated, the PAUSE button is enabled. If this button is actuated, the printer completes printing of any partially printed label and then cycles through inquiry steps 173 and 175. Actuating the CONTINUE button sets the status register of the random logic 103 such that inquiry 173 produces a negative response but inquiry 175 produces a positive response. Actuating the same PRINT button sets the status register of random logic 103 such that inquiry 175 produces a negative response but inquiry 173 produces a positive response, sequencing the printer through step 183 which results in a positive response to inquiry 175.

A positive response to the inquiry 175 then advances the printer operation to a step 185 wherein the ID counters are set. The printer logic scans the memory 84 for the start of data (SOD) code at a step 187. Upon detecting the start of data code the printer advances to a step 195 where it waits for an IDA code to appear, thereupon advancing to a step 197. Step 197 increments the IDA counters. When the ID data for one patient appears at the input buffer 123, the ROM 105 calls a subroutine from the ROM 107 to increment the patient ID counters. The contents of patient ID counters are compared with the contents of the patient ID registers in inquiry steps 201 and 203. If either inquiry 201 and 203 produce a negative response, indicating the patient ID register and patient ID counters do not contain the same bit pattern, the printer sequences back to inquiry step 195 to wait for the next ID mode word.

If both 201 and 203 produce a positive response the printer advances through a data storing step 207, an inquiry 209, a second data storing step 211 and an inquiry 213. During this sequence the patient ID is stored in the random-access-memory 109.

Upon completion of the inquiry 209 or 213 with a negative response, the memory 105 advances the printer into a sequence of inquiries 215, 217 and 219. If there is no external device data associated with the present patient, the sequence of operation advances through inquiries 215 and 217 to inquiry 219. The conditions of a negative response to the inquiry 215 or a positive response to the inquiry 217 will be discussed shortly. A positive response to the inquiry 219 advances the printer operation to step 227 wherein a register is set to denote the case of ID data followed immediately by note data. Upon completion of step 227, the printer sequences to a step 225 wherein the note data is placed in a temporary storage area in the RAM 109. The data storage step 225 may also be entered through step 223 any time a note mode word has been detected in the patient's data. When the printer operation has advanced to step 225, the patient ID has been stored in the RAM 109 and note data from memory 84 is transferred to the RAM 109 through the register 143. All data transferred from the memory 84 to the RAM 109 is transferred at the clock frequency of the acquisition unit 10.

A negative response to the inquiry 219 advances the printer operation to step 221 and the ROM 105 is addressed with operating instructions from the jump table. In step 221 the current data mode word is used to select an address from a jump table in ROM 105 for the purpose of causing a branch in the sequence to the step appropriate for processing the type of data indicated by the mode word. From step 221, a jump may be made to any of steps 281, 283, 291, 303, 319, 337, 353, or 355. Results of these jumps will be discussed.

Upon completion of the load data step 225, the sequence advances to an inquiry 229 and upon a negative response to inquiries 231 and 233 to a step 235. After completing the step 235, the printer operation advances to an inquiry 237 of FIG. 7b.

The inquiry 237 is also entered if the inquiry 215 produces a negative response. If the inquiry 215 produces a positive response and the inquiry 217 results in a positive response, then a register incrementing step 239 is entered and upon completion of this step the sequence moves to inquiry 237.

Still another sequence for entering the inquiry 237 is through a step 241 any time an external or external manual mode word is detected in the patient's data. Still another path for entering the inquiry 237 is when the inquiry 229 produces a positive response indicating that a word from the acquisition unit 10 is an external or external manual mode word whereupon the inquiry 243 is made. A negative response to the inquiry 243 enters the inquiry 237 directly and a positive response advances the sequence to a step 245 and through the step 239 to the inquiry 237.

If the word transferred from the memory 84 is identified as an external manual mode word, the sequence advances to a store data step 247 wherein the word from the memory 84 is transferred to the register 143 for storage in the RAM 109. Upon completion of the step 247, the sequence advances to an inquiry 251. A positive response to inquiry 251 advances the printer to a register incrementing step 253 which is the same as step 239. Following the step 253, a label stop code is loaded into the RAM 109 in a step 255 and then, a line stop code and column stop code are loaded into the memory 109 in a step 257. A column stop code indicates that all characters on the present row of the print drum which are to be printed on the current line of the label have been printed. A line stop code indicates that all characters to appear on one line of the label have been printed. A label stop code indicates that an entire label has been printed. Also during the step 257, the RAM input register 143 is cleared, whereupon the sequence advances to a step 261. Step 261 loads the trigger magnets controller 161. Following the step 261 an inquiry 263 is made to determine if the accessed address in the RAM 109 contains a column stop code. If not, the printer cycles from step 263 to inquiry 261 until all characters on the present drum row which are to appear on the current label line have been printed. This is indicated by the detection of a column stop code. The printer 16 then advances to an inquiry 259 wherein the RAM input register 143 is incremented and tested for the presence of a line stop code which would indicate that all characters on the present line of the label have been printed. Until this code is detected the printer cycles from inquiry 259 to step 261 until each row on the print drum has passed and the line stop code is detected. The printer then advances to inquiry 265 wherein the presence of the label stop code is tested. If not present, the printer cycles to step 257 to print additional lines of data until inquiry 265 detects the label stop code indicating that the entire label has been printed. The printer then advances to step 267 wherein the next label 18 in the strip is advanced until it enters the printer mechanism. The RAM is then cleared of patient data in step 269 and the sequence then returns to inquiry 175.

Returning to the inquiry 237, if the word under consideration in the memory 84 is not an external manual mode word, the sequence advances to an inquiry 271 (instead of the step 247) and upon a positive response thereto continues to the inquiry 251 and therefrom as explained. A negative response to the inquiry 271 advances the sequence to an inquiry 273 which returns the sequence to the load data step 225 upon a positive response and advances the sequence to an inquiry 275 from a negative response. A positive response to the inquiry 275 indicates that the word next to be transferred from the memory 84 is the end-of-data word and the sequence advances to a step 277 to set the status flip-flop and the sequence advances to an incrementing step 279. The step 279 increments the IDA registers. This step is also entered through a step 281 when an IDA mode word is detected.

The steps 277 and 279 are also completed any time an end-of-data mode word is used to address the read-only-memory 105 jump table.

Referring to FIG. 7c, a negative response to the inquiry 251 advances the printer sequence to an inquiry 285 and upon a positive response thereto advances to an inquiry 287 and then to an asterisk code storing step 289. The step 289 is also entered from a step 291 when the word to be transferred from the memory 84 is manually entered temperature data. The step 289 stores an asterisk code in the RAM 109 for printing on a label 18 to highlight manually generated data.

Following completion of the step 289, the printer sequence advances to a data storing step 293 wherein an inquiry of the content of the external register is made. The step 293 may also be entered from a step 303 when a temperature mode word is detected at the memory 84. A positive response to the inquiry of step 293 advances the printer to a data storing step 299 and then to a step 301. The step 301 is a step for loading the RAM 109 with data from an acquisition unit.

A negative response to the inquiry 285 sequences the printer to an inquiry 305 which again checks the condition of the external register. Following a negative response to the inquiry 305, the sequence advances through an inquiry 307 and then to a data storing step 315 either directly or through an asterisk data storing step 317. The step 317 for storing an asterisk code in the RAM 109 may also be entered through a step 319 if a respiration rate manual mode word is detected in the memory 84. In the step 315, data transferred from the memory 84 is stored in the RAM 109. This step is also entered from a step 337 when a respiration rate mode word is detected in the memory 84. Step 315 is completed by using the next mode word in the memory 84 to address the ROM 105 jump table to branch in accordance with the mode word.

A positive response to the inquiry 305 sequences the printer routine to an inquiry 339 and from the inquiry 339 directly to a data storing step 349 or through an asterisk code storing step 351. The asterisk code storing step 351 may also be entered from the step 353 when a pulse rate manual mode word is detected in the memory 84. The data storing step 349 is also entered from the step 355 when the pulse rate mode word is detected in the memory 84.

Primarily, data is stored in the RAM 109 from the acquisition unit 10 in the steps 301, 315 and 349. When manually generated data for the temperature, pulse rate and respiration rate are stored in the memory 84, an asterisk code is stored in the RAM 109 in the steps 289, 317 or 351.

Upon completion of the transfer of data from the acquisition unit 10 into the RAM 109, the print routine is entered. During the print routine, the printing mechanism sends three signals to the control circuitry. These are denoted as the printer reset signal and the TP and TL signals. The reset signal occurs once for each complete drum revolution of the printing mechanism and the TP and TL signals occur for each row of characters of the print drum. In a typical embodiment of the printer mechanism there are 16 rows of characters with each character identified by a code signifying its row and column location on the print drum. The TP signal occurs prior to the row it is associated with and the TL signal occurs at the end of the row with which it is associated. Actual printing of a character is completed by activating trigger magnets to drive a hammer against the print drum, causing the character in that row and column location on the print drum to be printed on the label 18. The trigger magnets are activated on the TP signal and deactivated on the TL signal.

Printing of a character is completed by transferring to the RAM input register 143 the code for a character at a particular row and column location and comparing the number in the register 143 with the data stored in the RAM 109, the comparison taking place in the comparator 141. Thus, the register 143 contains the code of the print drum line which will next be struck by the printer hammers (that is, the line on which the next set of characters to be printed is located). The print drum is constructed such that the data stored in the RAM 109, when the same as the print drum line code, is the correct character to be printed.

A character is printed by shifting a logic ONE signal into a twenty bit serial input, parallel output shift register in the trigger magnets controller 161. If the code at a particular address in the RAM 109 and the code in the register 143 are the same, a logic ONE is shifted into the shift registers. If the codes are different, a logic ZERO is shifted and the hammer magnets remain deactivated. Each shift register output controls a trigger magnet driver which is switched on when the shift register output goes to logic ONE.

As an example, assume the data to be printed is T102.5* starting in column one on the label 18. Starting at line zero on the print drum, the shift registers of the trigger magnets controller 161 will contain all logic ZEROES with the exception of a logic ONE in column 3 which will cause the number "0" to be printed on the label 18. This is because the number stored in the third location of the RAM 109 contained a code representing the number "0" in the data T102.5*. Next, the register 143 is incremented to a code representing the number "1". When the second location in the RAM 109 is compared to the contents of the register 143 in the comparator 141, a match will result and a logic ONE will be shifted into the trigger magnets controller 161 thereby causing the number "1" to be printed in column 2 on the label 18. This sequence continues with codes representing the numbers 2–9 and other characters shifted into the register 143 and compared with the various locations of the RAM 109. When the code representing the letter "T" is shifted into the RAM input register 143, a match is made in column one since the code for the letter "T" is now in the register 143. Thus, a logic ONE will be shiftd into column one of the trigger magnets controller 161 to control the appropriate trigger magnet causing the letter "T" to be printed in column one of the label 18. The other characters are printed in a similar manner as is the asterisk.

After completely printing the data for a particular patient ID, the next label is incremented under the print drum, the printer sequences to inquiry 175, and data for the next patient ID is printed on the label 18. This continues for each patient ID until all the data transferred from the acquisition unit 10 to the RAM 109 is printed on a label 18. Following the printing of data for the last patient ID, the print sequence returns to the idle mode.

If during the operation of a printing sequence the label supply is depleted or a malfunction occurs in the print mechanism, the printer may be halted by use of the PAUSE button to await further instructions to proceed. When reactivated with the CONTINUE button, the sequence of printing begins where previously terminated. If during this shut down another acquisition unit is inserted into the printer, the data therein cannot be read into the RAM 109 until the data in the previously inserted acquisition unit has been printed on the labels 18.

Following completion of the printing of all the data in a particular acquisition unit, and upon its removal from the chute 40 or 42, the memory 84 is cleared except for a start-of-data word at one location and an end-of-data word at the next location. The acquisition unit is then ready to be used again for acquiring and storing additional temperature, pulse rate, and respiration rate data from patients up to the limit of the memory 84.

While only one embodiment of the invention, together with modifications thereof, has been described in detail herein and shown in the accompanying drawings, it will be evident that various further modifications are possible without departing from the scope of the invention.

What is claimed is:

1. A respiration data acquisition, conversion and display system comprising:
    a respiration rate sensor having a resistance varying cyclically with respiration rate;
    first means connected to the respiration rate sensor to generate a series of electrical output pulses having a repetition rate related to the cyclic change in the resistance of the respiration rate sensor;
    means for generating a train of clock pulses,
    a counter receiving the clock pulses, and triggered into an "on" state by a first specified number of output pulses of said first means and triggered into an "off" state by a second specified number of subsequent output pulses of said first means and where a total count registered represents the time period of the second specified number of output pulses representing the cyclic changes in the resistance of the respiration rate sensor;
    a divider receiving the total count of the counter wherein the numerator of the divider is a scaling constant and the denominator of the divider is the total count of the counter and where the output of the divider represents the average respiration rate in respiration cycles per minute; and
    display means connected to said divider for displaying the respiration rate.

2. A respiration data acquisition, conversion and display system as set forth in claim 1 wherein said counter comprises:
    a first register connected to the first means for generating an "on" signal upon receiving the first specified number of output pulses from the first means and for generating an "off" signal upon receiving the second specified number of subsequent output pulses from the first means; and
    a second register receiving the clock pulses, and triggered into an "on" state and an "off" state by the first register, and where the total count registered represents the time period of the second specified number of output pulses representing the cyclic changes in the resistance of the respiration rate sensor.

3. A respiration data acquisition, conversion and display system as set forth in claim 1 wherein the first means comprises:
    voltage generating means connected to the respiration rate sensor to generate a voltage varying with the cyclic variation in the resistance thereof;
    an amplifier connected to the voltage generating means to amplify the varying voltage thereof;
    a Schmitt trigger circuit connected to the output of said amplifier and responsive to the amplified varying voltage thereof to generate a series of output pulses having a repetition rate related to the cyclic change in the resistance of the respiration rate sensor; and a one-shot multivibrator connected to the Schmitt trigger circuit responsive to the output pulses thereof to generate a series of output pulses of uniform duration at a repetition rate related to the cyclic change in the resistance of the respiration rate sensor.

* * * * *